(12) United States Patent
Campbell et al.

(10) Patent No.: US 11,747,259 B1
(45) Date of Patent: Sep. 5, 2023

(54) TEMPERATURE ADJUSTED MODULATION OF A SIGNAL CENTER WAVELENGTH IN LIQUID ABSORPTION SPECTROSCOPY

(71) Applicant: Airware, Inc., Newbury Park, CA (US)

(72) Inventors: Thomas G Campbell, Newbury Park, CA (US); Jacob Y Wong, Goleta, CA (US)

(73) Assignee: AIRWARE, INC., Newbury Park, CA (US)

( * ) Notice: Subject to any disclaimer, the term of this patent is extended or adjusted under 35 U.S.C. 154(b) by 0 days.

(21) Appl. No.: 18/114,414

(22) Filed: Feb. 27, 2023

Related U.S. Application Data

(63) Continuation-in-part of application No. 17/227,789, filed on Apr. 12, 2021, now Pat. No. 11,604,138, which is a continuation of application No. 17/073,297, filed on Oct. 17, 2020, now Pat. No. 10,976,243, which is a continuation-in-part of application No. 16/600,466, filed on Oct. 12, 2019, now Pat. No. 10,983,046, which is a continuation-in-part of application No. 16/359,350, filed on Mar. 20, 2019, now Pat. No. 10,473,586, which is a continuation-in-part of application No. 16/056,531, filed on Aug. 7, 2018, now Pat. No.
(Continued)

(51) Int. Cl.
| | |
|---|---|
| *A61B 5/145* | (2006.01) |
| *A61B 5/1455* | (2006.01) |
| *A61B 5/00* | (2006.01) |
| *G01N 15/06* | (2006.01) |
| *G01N 33/487* | (2006.01) |
| *G01N 21/31* | (2006.01) |
| *G01N 21/3577* | (2014.01) |
| *G01N 21/21* | (2006.01) |
| *G01N 33/49* | (2006.01) |

(52) U.S. Cl.
CPC ........... *G01N 15/06* (2013.01); *A61B 5/0075* (2013.01); *A61B 5/1451* (2013.01); *A61B 5/1455* (2013.01); *A61B 5/14532* (2013.01); *G01N 21/3151* (2013.01); *G01N 21/3577* (2013.01); *G01N 33/487* (2013.01); *A61B 5/0062* (2013.01); *A61B 2562/0238* (2013.01); *G01N 21/21* (2013.01); *G01N 33/49* (2013.01); *G01N 2015/0693* (2013.01); *G01N 2021/3148* (2013.01); *G01N 2201/10* (2013.01)

(58) Field of Classification Search
CPC ... A61B 5/0062; A61B 5/0075; A61B 5/1451; A61B 5/14532; A61B 5/1455; A61B 2562/0238; G01N 15/06; G01N 21/21; G01N 21/3151; G01N 21/3577; G01N 33/487; G01N 33/49; G01N 2015/0693; G01N 2021/3148; G01N 2201/10
See application file for complete search history.

(56) References Cited

U.S. PATENT DOCUMENTS 6,509,567 B2 * 1/2003 Boudet ................ G01N 21/314
250/575

\* cited by examiner

*Primary Examiner* — Mark R Gaworecki
(74) *Attorney, Agent, or Firm* — Roy L Anderson

(57) ABSTRACT

Increased precision for liquid absorption spectroscopy, especially for in vivo samples of human analytes, is obtained by varying the signal or signal and interference central wavelengths when the temperature of the sample site varies beyond a selected threshold used for determining standardized signal or signal and interference central wavelengths. The amount of variance for a central wavelength of the signal beam which includes 1,150 nm is approximately 2 nm or less.

14 Claims, 22 Drawing Sheets

Related U.S. Application Data

10,241,044, which is a continuation-in-part of application No. 15/785,829, filed on Oct. 17, 2017, now Pat. No. 10,041,881, which is a continuation-in-part of application No. 15/644,775, filed on Jul. 8, 2017, now Pat. No. 9,823,185, which is a continuation-in-part of application No. 15/594,418, filed on May 12, 2017, now Pat. No. 9,726,601, which is a continuation-in-part of application No. 15/444,136, filed on Feb. 27, 2017, now Pat. No. 9,678,000, which is a continuation-in-part of application No. 15/358,873, filed on Nov. 22, 2016, now Pat. No. 9,606,053.

Fig. 3. Absorption coefficient from 550 to 800 nm adjusted at 685 nm to the value of Tam and Patel (1979). The curves represent absorption at temperatures of 5, 10, 15, 21, 25, and 30°C as read from bottom to top at 750 nm.

| Temperature (°C) | Absorbance |
|---|---|
| 25 | 1.418 |
| 40 | 1.403 |
| 60 | 1.390 |
| 80 | 1.372 |

TEMPERATURE ADJUSTED MODULATION OF A SIGNAL CENTER WAVELENGTH IN LIQUID ABSORPTION SPECTROSCOPY

CROSS-REFERENCE TO RELATED APPLICATIONS

The present invention is a continuation-in-part application of U.S. Ser. No. 17/227,789, filed Apr. 12, 2021, which is a continuation application of U.S. Ser. No. 17/073,297, filed Oct. 17, 2020, which is a continuation-in-part application of U.S. Ser. No. 16/600,466, filed Oct. 12, 2019, which is a continuation of U.S. Ser. No. 16/359,350, filed Mar. 20, 2019, which was a continuation-in-part application of U.S. Ser. No. 16/056,531, filed Aug. 7, 2018, which is a continuation-in-part of U.S. Ser. No. 15/785,829 filed Oct. 17, 2017, which is a continuation-in-part of U.S. Ser. No. 15/644,775 filed Jul. 8, 2017, which is a continuation in part of U.S. Ser. No. 15/594,418 filed May 12, 2017, which is a continuation-in-part application of U.S. Ser. No. 15/444,136 filed Feb. 27, 2017, which is a continuation-in-part application of U.S. Ser. No. 15/358,873, filed Nov. 22, 2016, the disclosures of all of which are specifically incorporated herein by reference.

FIELD OF THE INVENTION

The present invention relates to liquid absorption spectroscopy.

BACKGROUND OF THE INVENTION

The present invention seeks to advance the field which its inventors have pioneered, especially for use in detecting target molecules, such as glucose, in liquid samples, such as in vitro mammalian tissues.

More particularly, the present invention seeks to enhance precision measurements through novel modulation of center wavelengths so as to adjust for temperature variations of samples from a standardized temperature.

This and further objects and advantages will be apparent to those skilled in the art in connection with the figures and the detailed description of the invention set forth below.

SUMMARY OF THE INVENTION

The present invention is generally directed to systems and processes which adjust a signal center wavelength for a signal beam bandwidth, or a signal center wavelength for a signal beam bandwidth and an interference central wavelength for an interference beam bandwidth, to account for temperature variations of a liquid sample from a temperature used to standardize the signal central wavelength or the signal central wavelength and the interference central wavelength, when such wavelengths are used in absorption spectroscopy processes.

The object of the present invention is to provide an improved system and process for detection of molecules in a liquid medium.

This and further objects and advantages will be apparent to those skilled in the art in connection with the figures and the detailed description of the invention set forth below.

BRIEF DESCRIPTION OF THE DRAWINGS

FIG. 2 illustrates some ideal transmissive sensing sites for a human body while

DETAILED DESCRIPTION OF THE INVENTION

Figure 1:
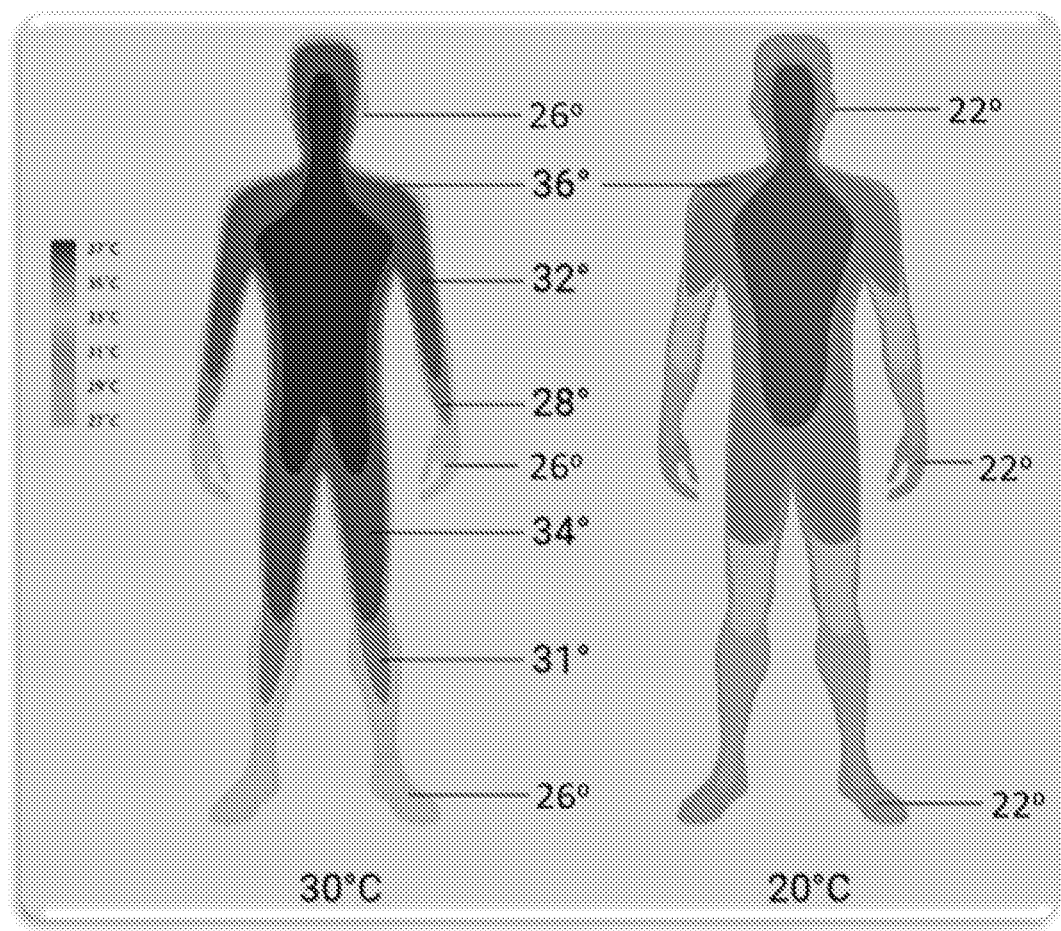
FIG. 1 is a thermal mapping profile of a human form with one held in a 30° C. environment and the other in a 20° C. environment.

Before addressing the merits of the present invention, it is worthwhile to review some of the disclosures the inventors have already made in liquid absorption spectroscopy processes, to gain a better understanding of the present invention.

U.S. Pat. No. 9,606,053 (2017) discloses an NDIR method which significantly suppresses scattering noise attributable to the much higher molecular density which is encountered in a liquid medium, as opposed to a gaseous medium. The method utilizes alternating and successively pulsing infrared radiation from signal and reference sources which are multiplexed and collimated into a single pulsed beam directed through the liquid sample. The pulse frequency is set sufficiently fast so as to provide almost the same molecular configuration to both the signal and the reference beams. The scattering noise encountered by both beams is effectively the same and can be significantly reduced through processing the ratio of their respective pass-through outputs.

U.S. Pat. No. 9,678,000 discloses using an NDIR method to detect glucose in a liquid medium. Glucose has an overtone absorption band located at 1,150 nm which can be used as the center wavelength for the signal beam. This absorption band is desirable because it has a water absorption coefficient of no greater than ~1.0 cm$^{-1}$, which is especially preferred, as it helps to minimize effects created by water absorption. A reference beam wavelength of 1,064 nm, where there is no glucose molecule absorption, can be used as the center wavelength for the reference beam.

U.S. Pat. No. 9,726,601 discloses an improved NDIR method for determining the concentration of targeted molecules labeled M in a liquid medium admixed with interfering molecules labeled $M_J$, which uses an additional interference radiation source besides those of the signal and reference to significantly reduce the interference noise. U.S. Pat. No. 9,823,185 (2017) discloses an improvement to this method with suppression of both scattering and absorption interference noise (AIN) via a reflection detection technique.

U.S. Pat. No. 10,475,586 discloses a signal source, an interference source, a reference source, a multiplexer and a collimator to pulse radiation in a pulsed beam which is detected by a detector as is described in greater detail in U.S. Pat. Nos. 9,606,053 and 9,823,185. The signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band; at least one interfering molecule $M_J$ absorbs radiation at the signal wavelength; and the signal source, the interference source and the reference source are each pulsed at a preselected frequency of at least N Hz which is sufficiently fast so that a given molecule of the targeted molecule M or said at least one interfering molecule $M_J$, will not pass in and out of the liquid sampling matrix within the preselected frequency.

Figure 8:
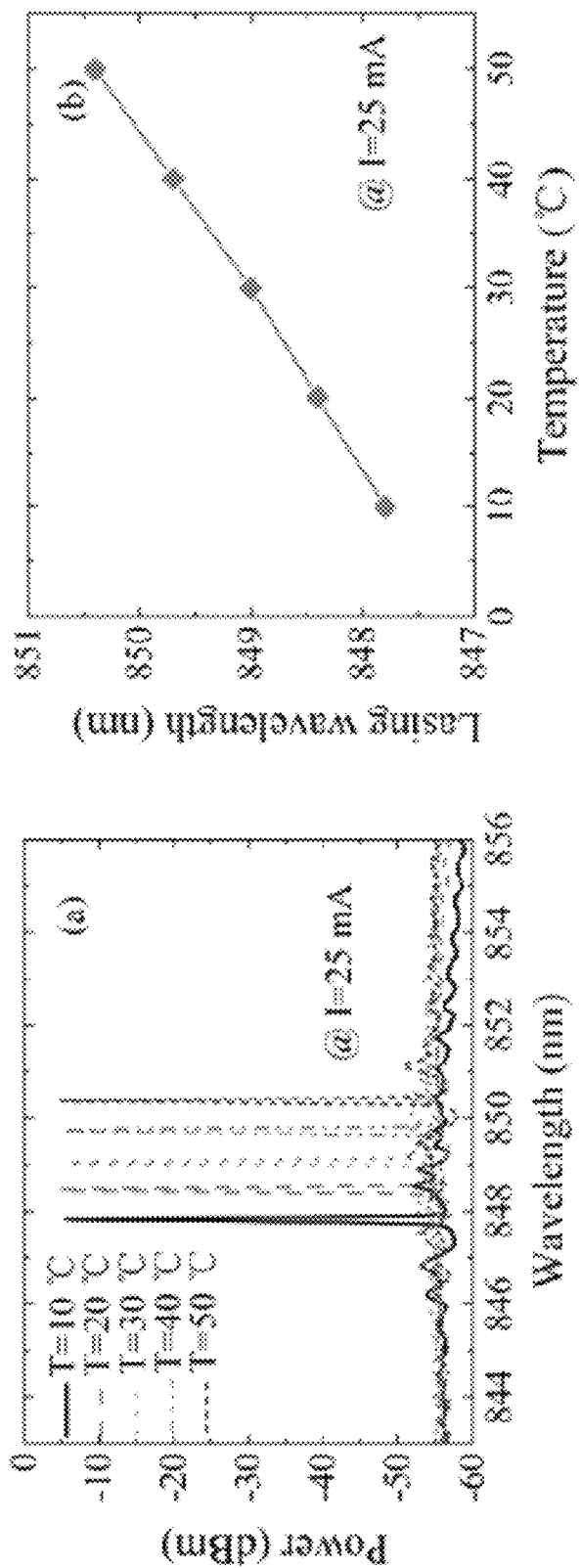
FIG. 8 illustrates how a laser's center wavelength will shift up as temperature increases while keeping the input current constant.

FIG. 8 in U.S. Pat. No. 9,823,185 illustrates an optical setup of a Signal diode laser, a Reference diode laser and an Interference diode laser which are driven alternately and successively in groups of two by a 3-channel high speed waveform generator. In this figure, output 26 of Signal diode laser 27 is driven alternately and successively with output 28 of Reference diode laser 29 as a pair; meanwhile output 30 of Interference diode laser 31 is driven alternately and successively with output 28 of Reference diode laser 29 as another pair. The rest of the optical and electronic processing system setup for a three-diode laser system to suppress both scattering noise and AIN is the same as the two-diode laser system disclosed in U.S. Pat. No. 9,606,053 for suppressing just the scattering noise.

U.S. Pat. No. 10,041,881 discloses an improved NDIR method for liquids in which scattering noise is reduced and an Absorption Interference Noise (AIN) is suppressed with a reflection technique.

U.S. Pat. No. 10,241,044 discloses a process for deciding the validity of the calibration curve for targeted molecules $M_G$ in a liquid sample with interfering molecules. This value can further be used to adjust the calibration curve via a parameter linking the transmittances measured at the signal and interference wavelength channels in order to assure its validity.

U.S. Pat. No. 10,473,586 discloses different sample capture techniques to enhance the accuracy, precision and reliability of measurements with our inventive Direct Infrared Laser Absorptive Scattering Technique (DILAST) sensors.

U.S. Pat. No. 10,976,243 discloses configuring a sampling volume so that sampling error caused by changes of a targeted molecule passing in an out of the sample volume is approximately the same or less than a measurement error caused by an accuracy limit of the electronic components and the optical elements.

It is with this background that the present invention will now be discussed.

A particular challenge to optically monitoring concentration of one or more analytes in a liquid sample or mammalian tissue by absorption spectroscopy lies with temperature variation. The instant invention improves precision by establishing a methodology and system to characterize temperature effects on focus analytes upper or peak absorption wavelengths, and then adjust the interrogation light emitter peak or center wavelength(s) to match. In so doing, the spectroscopic absorption function is maximized while minimizing excess noise generated by non-desired absorption effects and from Rayleigh, Mie, and geometric scattering effects. Various techniques for modulating the light emitter source are available with general rules that higher current translates to a higher wavelength and higher temperature also translates to a higher wavelength. Other techniques include acousto-optic, magneto-optic, Surface Plasmon Resonance, and variable pressure gaseous chambers. The most precise, smallest, & lowest cost methods by electro-optics and thermos-optics appear to be the most desirable.

Optical monitoring of analytes in a liquid is immensely simplified when the liquid sample can be maintained at a specific temperature for all interrogations. This is not the case when monitoring human skin or tissue. Humans exist in a world of dynamic temperature conditions. So, in addition to the complex nature of human tissue being a turbid medium composed of different cell types and protein-rich extracellular matrix, which strongly impact the propagation of light, the effects of temperature variability in skin are addressed and a new electro-optical control system is described to manage the input energy and output detection that enable a higher level of sensing precision.

Understanding both the environment and the interaction of the sample or skin under interrogation is the necessary starting point of the present invention. And within the human condition, a wide variation of thermal responses can be expected depending on an individual's age, height, weight, and general physical condition. In FIG. 1 we see a thermal mapping profile of a human form with one held in a 30° C. environment and the other in a 20° C. environment. Extremities are more affected by temperature changes as the human body's ability to control its temperature is focused on maintaining a stable core temperature at the expense of extremities.

Figure 2:
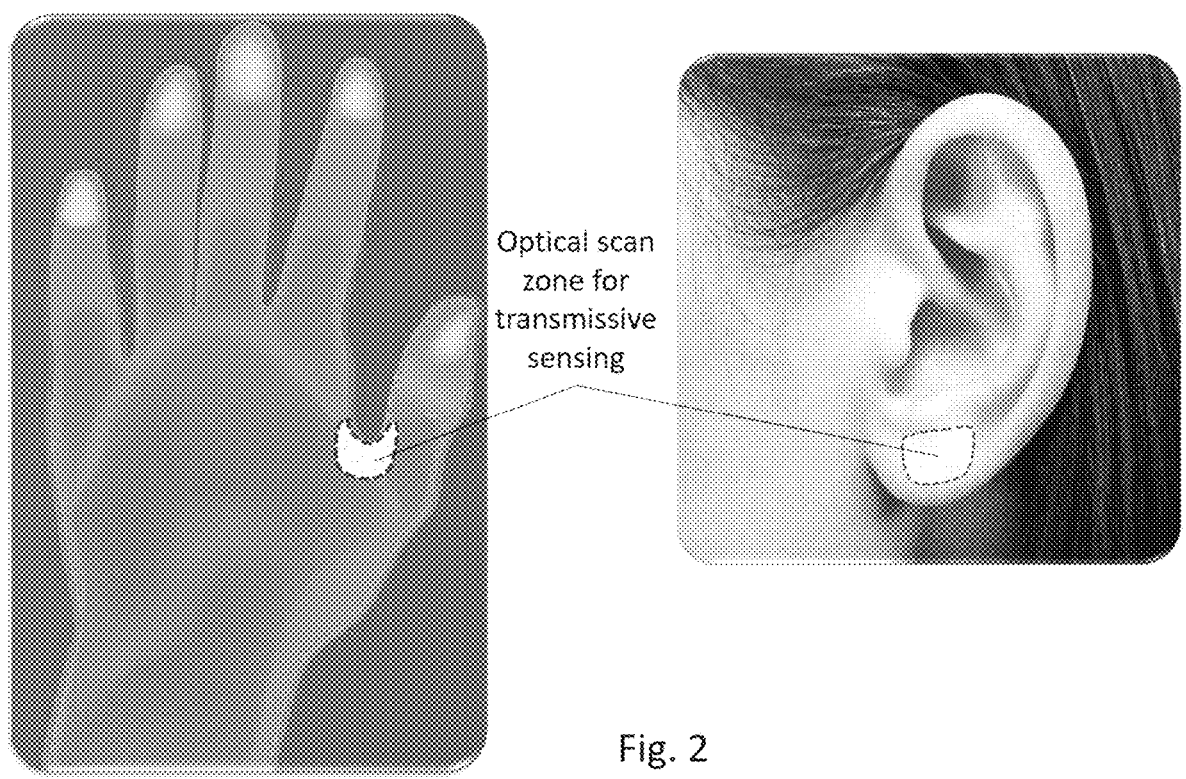

In accordance with the present invention, optical sensing methodology can be driven to adapt to variations in skin temperature at the sensing site. The methodologies, in general, are similar for transmissive sensing and reflective sensing modes. The ideal transmissive sensing sites at the hand web and ear lobe, being the most exposed to atmospheric conditions, will have the greatest variation in skin temperature. FIG. 2 illustrates these typical transmissive sensing sites on the human body.

These ideal sensing sites are also extremities subject to the widest temperature excursions. As with all scientific instruments, there are prescribed operating ranges. Yet still, in delivering technology that is designed to accompany humans through their daily lives, the present invention aims to offer systems that permit use with the widest range of allowable operating conditions as possible.

Figure 3:
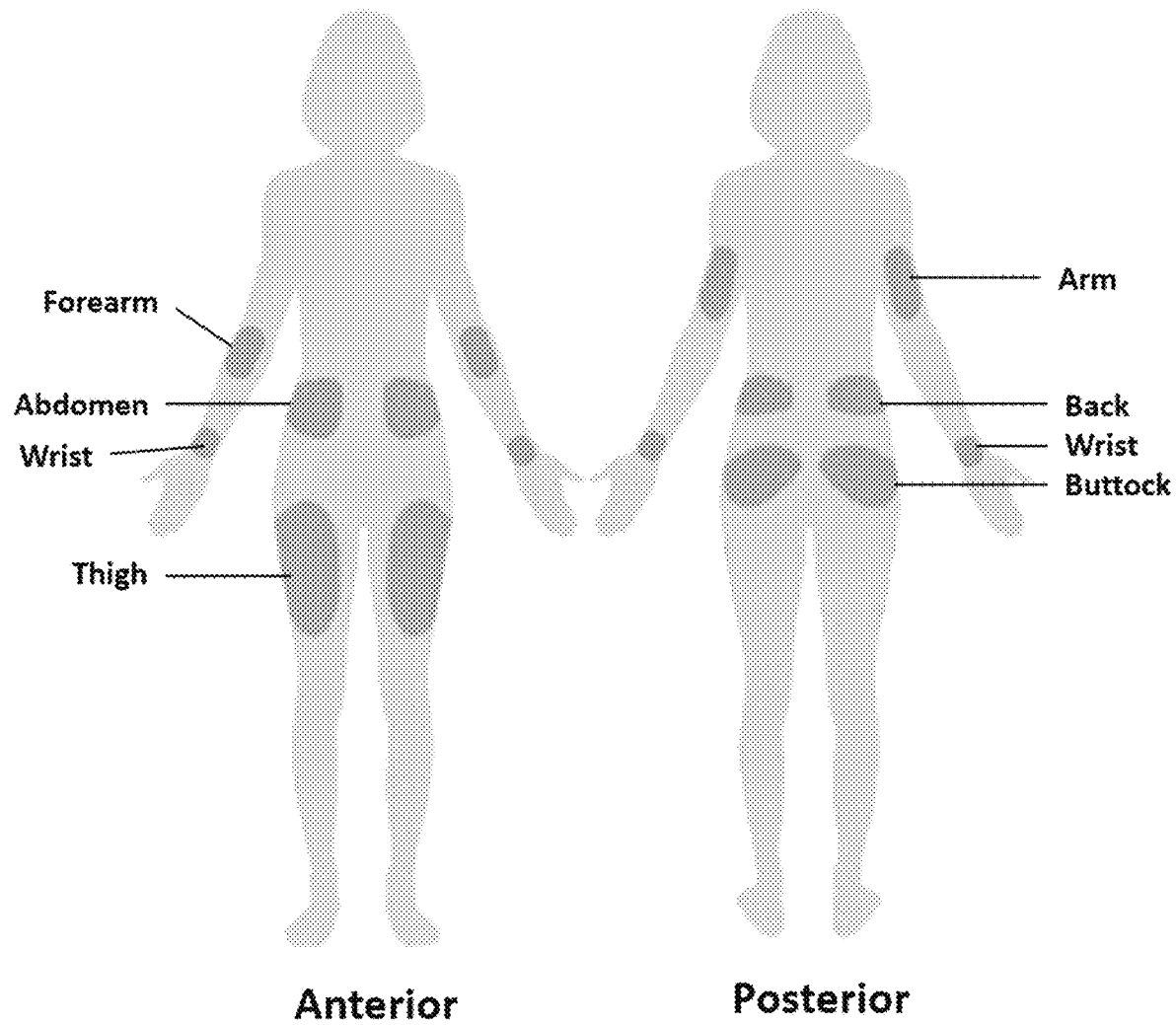
FIG. 3 illustrates some reflective sensing sites for a human body.

Another set of interrogation sites become available through reflective sensing as shown in FIG. 3. At most of these locations, reflective sensing can be accomplished under protective clothing that minimizes exposure to hot and cold. Additionally, most of these ideal reflective sensing sites are closer to the body's core where temperatures tend to be more stable than the extremities. Both clothing and relative position to the body's core simplify the analyte measurement task.

Knowing that there are uncontrolled temperature variables in human sensing and categorizing them as to extremity or core body location, one can now address skin temperature monitoring and electro-optical methodologies to adjustment of our absorption spectroscopy system that relies on "analyte specific absorption peaks" or ASAPs. We compare the measured intensity of light that passes through a sample or skin at two wavelengths. One wavelength is matched to our target analyte absorption peak and the other wavelength is matched to a relative null zone for absorption such that the ratio of these two measurements cancels out common Rayleigh, Mie, and geometric scattering noise delivering a precision value for just the target analyte as described in U.S. Pat. Nos. 9,606,063, 9,678,000, 9,726,601, 9,823,185, 10,241,044, 10,473,586, and 10,983,046.

It has long been known that temperature affects the absorption coefficient of water at the harmonics of the stretching of the O—H bond (Collins 1925; Luck 1963; Tam and Patel 1979). Effects of salinity on the O—H bond are manifested in the reflectance (Hirschfeld 1985) and Raman scattering (Georgiev et al. 1984). Sullivan (1963) showed that salinity affects the absorption of water in the near-IR. The formation of tetrahedral-shaped hydrogen-bonded macromolecules of water are related to temperature and salinity with demonstrated changes in optical absorption of water at harmonics of the O—H bond stretching frequency (Walrafen 1967; Whetsel 1968). These hydrogen bonded water macromolecules break up with increasing temperature and salinity with accompanying increases in optical absorption.

In order to maintain high accuracy of the measurement system of the present invention, optoelectronics are modulated to shift the narrow band emitter energy to match ASAPs over a range of typical thermal living conditions. The shifts in wavelength are relatively small (in the approximate range of up to a couple of nm) but important for precision sensing. Per one study of the dynamics of the water absorption peaks investigated at three wavelengths of water, absorption coefficients decreased for all three with increasing temperature, i.e., the absorption peak at 1.94 μm at 22° C. shifts to 1.92 μm at 70° C. Reference: Temperature dependence of the absorption coefficient of water for mid-infrared laser radiation E. Duco Jansen MSc, Ton G. van Leeuwen PhD, Massoud Motamedi PhD, Cornelius Borst MD, PhD, Ashley J. Welch PhD First published: 1994 https://doi.org/10.1002/lsm.1900140308Citations: 136.

Figure 4:
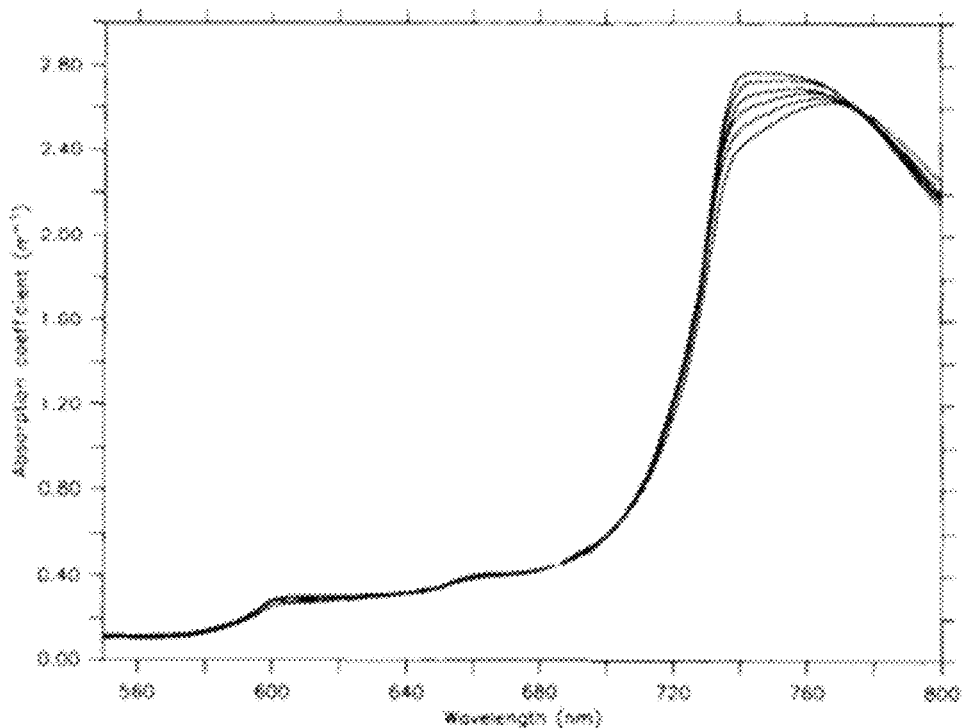
FIG. 4 is a graph showing the effects of temperature change on the absorption coefficient for a salt-water sample with a salinity of approximately 29%.
Figure 5:
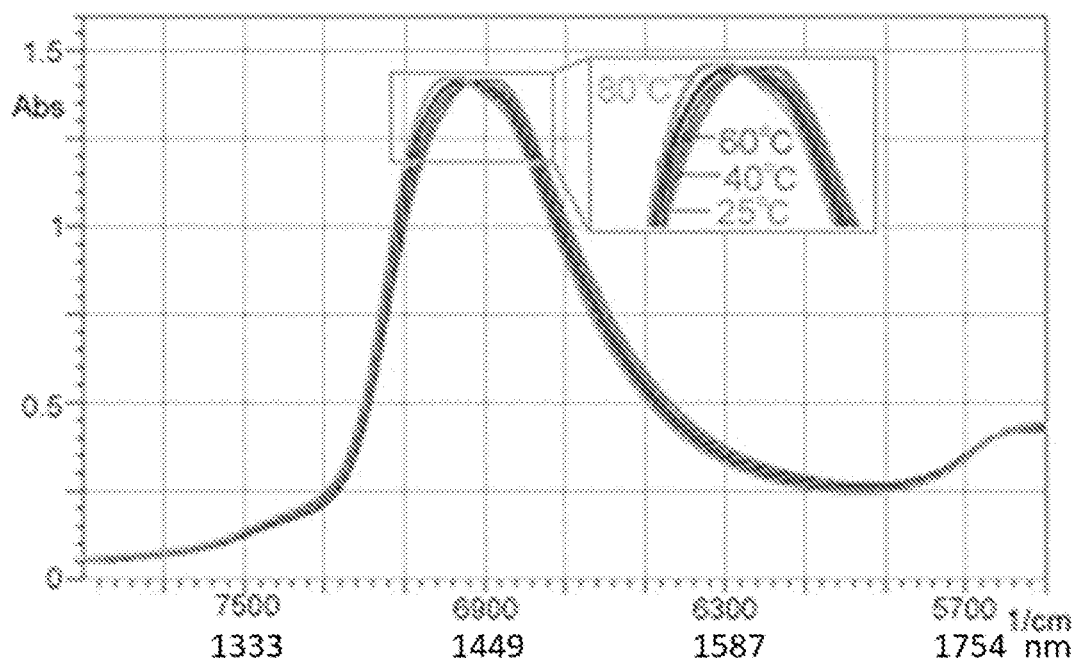
FIG. 5 is a graph showing the peak wavenumber of water over a temperature range.

As humans have a salty composition, it was decided to look to the analysis of a salt-water sample with a salinity of approximately 29 percent that was prepared using an aquarium salt mix and examined over a temperature range of 5° C. to 30° C. In laboratory experiments at the 750-nm absorption maximum of water, absorption increased significantly with temperature as shown in FIG. 4. The absorption maximum shifts toward 745 nm with increasing temperatures. Limnol. Oceanogr., 38(I), 1993, 188-1920 1993, by the American Society of Limnology and Oceanography, Inc. Temperature-dependent absorption of water in the red and near-infrared portions of the spectrum Pegau_and_Zaneveld_Limnol_Oceanogr_1993.pdf Shimadzu published in their Application News No. A365 precision data illustrating not only the peak wavelength shift with temperature, but also the related absorbance values. The absorbance value of water decreases with increasing temperature. Any optical absorption measurements involving water as a major species in a complex liquid such as skin should take into account these phenomena. FIG. 5 presents the spectra of water acquired over a temperature range of 25° C. to 80° C. And, while this is an overly broad temperature range with respect to what humans might encounter, it presents precision data for the magnitude of the absorbance effect with respect to temperature.

Absorption peaks in the infrared spectrum are narrow as a result of changes in vibrational energy only while absorption peaks in the ultraviolet and visible spectrum are relatively wide due to changes involving the vibrational, rotational and electronic energy levels together.

Absorption spectroscopy is the primary optical interaction that we exploit to measure our ASAPs of interest in samples or skin quantified by the ratio of reference wavelength and the target analyte wavelength absorptions that represent an absorption coefficient that we map to known concentrations or by calibration performed on human users.

Figure 6:
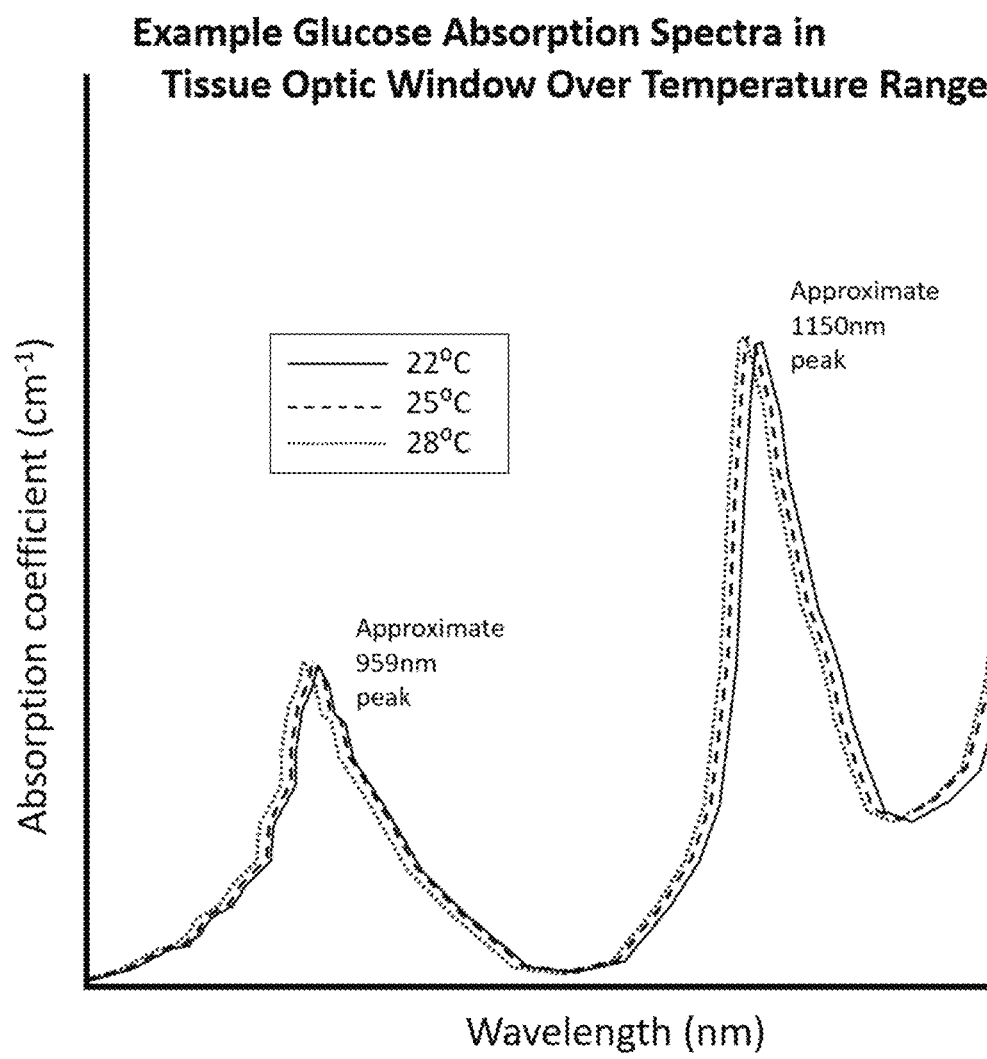
FIG. 6 is a graph showing how the spectral shift of the glucose molecule in water occurs with increasing temperature.

Focusing upon one analyte, FIG. 6 presents an example typical of how the spectral shift of the glucose molecule absorption in water occurs with increasing temperature. As absorption spectroscopy looks for the absorption at the highest values or absorption peaks, the requirement to shift our interrogation light emitting source central wavelength to match temperature related analyte absorption peaks becomes important to optimize sensor accuracy for analyte concentration measurement.

Our analyte sensing invention involves matching the real-world absorption spectra dynamics to effective operation of our light emitting sources such that peak absorptions track with peak sensor emissions.

In one embodiment, the preferred method of driving our narrow band lasers employs very low noise current drivers that are pulsed by way of a voltage input pattern. A key element of this particular system, to maintain very low system noise, is to hold the laser at its threshold current, pulsing only up to the operational range. In so doing, noise is minimized by not having the laser drop all the way down to its shutdown condition and then having to be brought back up to its operating condition for each output pulse.

Stability of the current source laser driver is critical to low noise operation as the drive current influences the laser center wavelength. And temperature is an important factor to consider for maintaining stability of both the laser driver current sources as well as the laser devices.

Each of the lasers' center wavelengths will shift with temperature according to the following laws:
1) Kirchoff's Law: When an object is at thermal equilibrium, the amount of absorption will equal the amount of emission.
2) Stephan Boltzmann Law: The hotter an object becomes the more infrared energy it emits.
3) Wien's Displacement Law: The wavelength at which the maximum amount of energy is emitted becomes shorter as the temperature increases.
4) Planck's Equation: Describes the relationship between spectral emissivity, temperature and radiant energy showing that peak energy shifts towards shorter wavelengths as the temperature increases.

These laws impact on both peak absorption band of the target and interfering analytes in the sample or skin as the temperature shifts as well as operation of our light emitting sources.

Figure 7:
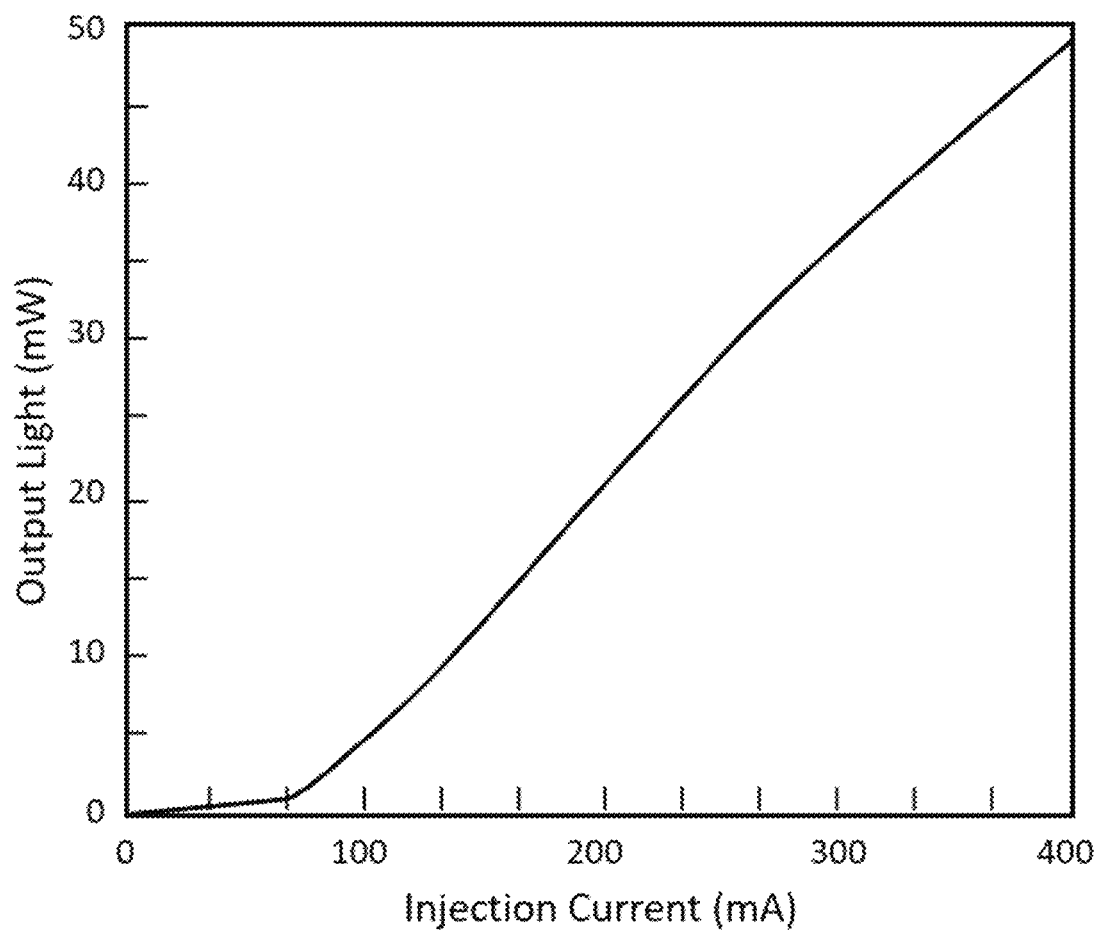
FIG. 7 is an L-I curve illustrating a laser diode's Light Output Power (L) response to Injected Current (I).

For our precision sensing purposes, an important characteristic for laser diodes as one choice of light emitting sources, is the laser diode's Light Output Power (L) response to Injected Current (I), presented in FIG. 7 as the L-I curve. The L-I curve demonstrates the threshold current, threshold current density, and differential responsivity. These values determine operational parameters such as the current at which lasing begins, the drive current for a specific laser power, as well as the maximum current the device can handle. And for our precision absorption spectroscopy, the drive current influences the laser's center wavelength. The sensitivity of laser diodes to injected current reveals the importance of driving with by a stable current source.

Within our narrow band optical emitter sensor system, we have a number of tools to manage the physics of how our light emitters will shift in wavelength with temperature. With semiconductor-based lasers, the bandgap of a semiconductor changes with temperature. At higher temperatures, the band gap decreases and the energy of the emitted photons also decreases making the effective emitted wavelength larger. This unfortunately shifts the wavelength up while a temperature increase of the sample or skin shifts the absorption peak of target analytes within down in wavelength. Standard practice to precisely control semiconductor-based light emitters employs thermo-electric coolers or TECs. Thermoelectric cooling is based upon the Peltier effect or thermoelectric phenomenon of the transfer of heat energy between two materials when an electric current passes through. The Peltier effect results in the addition or removal of heat proportional to the current flow. Reasons for using TECs are their small size, controllability, and lack of any moving parts. A major consideration, however, is availability of a sufficient, and preferably local, thermal sink to which excess heat or cold can be directed.

In addition to thermal management of the light emitter module itself, there are a number of electronic control variables that can be applied to manage the effective wavelength output.

FIG. 8 is representative of how a laser's center wavelength will shift up as temperature increases while keeping the input current constant which is published at Pengfei Zhang, Can Liu, Minwen Xiang, Xiang Ma, Gongyuan Zhao, Qiaoyin Lu, John F. Donegan, and Weihua Guo, "850 nm GaAs/AlGaAs DFB lasers with shallow surface gratings and oxide aperture," Opt. Express 27, 31225-31234 (2019), the disclosure of which is specifically incorporated herein by reference. This is an example of wavelength control by modulation of the TEC temperature. Of course, for our very precise sensor operation, we studiously avoid conditions where the constant current would create a heat build-up in the laser causing it to mode hop.

Laser diode controllers have temperature sensors and thermoelectric devices with feedback loops to keep the temperature constant, or to tune the diode laser to a specific wavelength.

Figure 9:
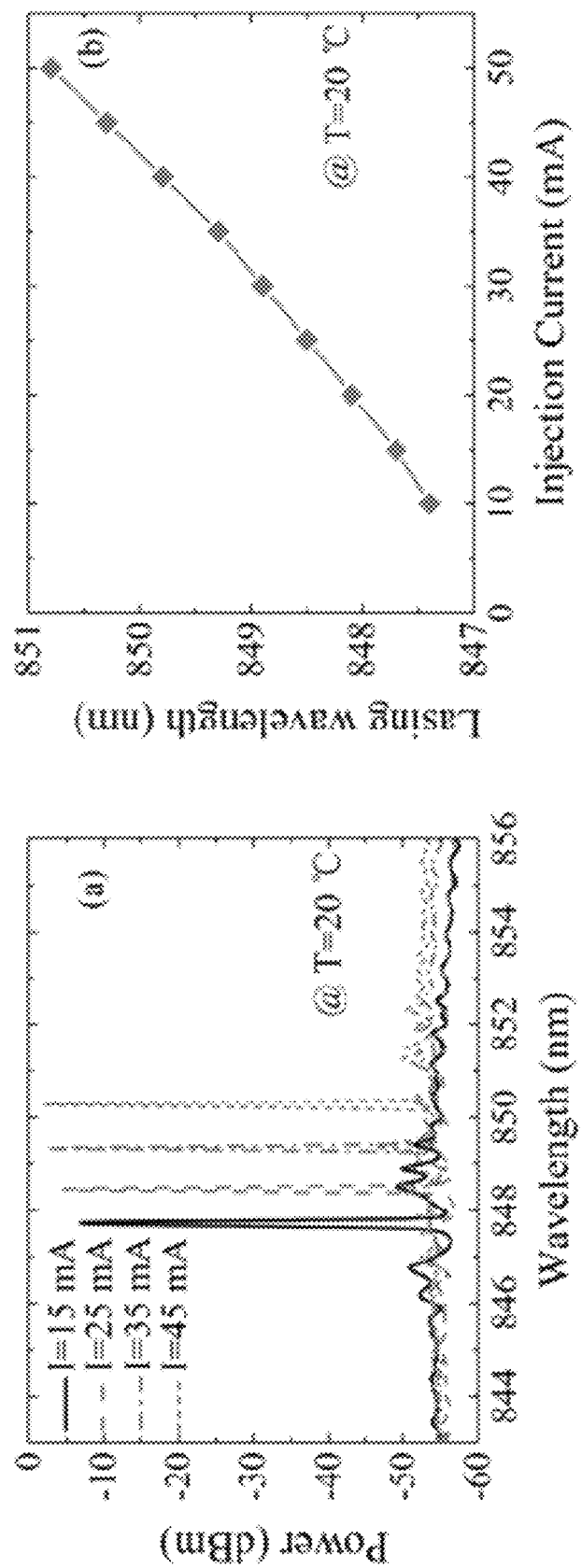
FIG. 9 illustrates how increasing the injection current shifts a light emitter's center wavelength.

Modulating the injection current is another option to control the light emitter output. As seen in FIG. 9, increasing the injection current from 15 mA up to 45 mA shifts the light emitter center wavelength from 847.7 nm up to 850.3 nm. This is an example of single-mode laser operation where increasing current affects the active region by narrowing the band gap and increasing the refractive index. FIG. 9 is published at Pengfei Zhang, Can Liu, Minwen Xiang, Xiang Ma, Gongyuan Zhao, Qiaoyin Lu, John F. Donegan, Weihua Guo, "850 nm GaAs/AlGaAs DFB lasers with shallow surface gratings and oxide aperture," Opt. Express 27, 31225-31234 (2019), the disclosure of which is specifically incorporated herein by reference.

Figure 10:
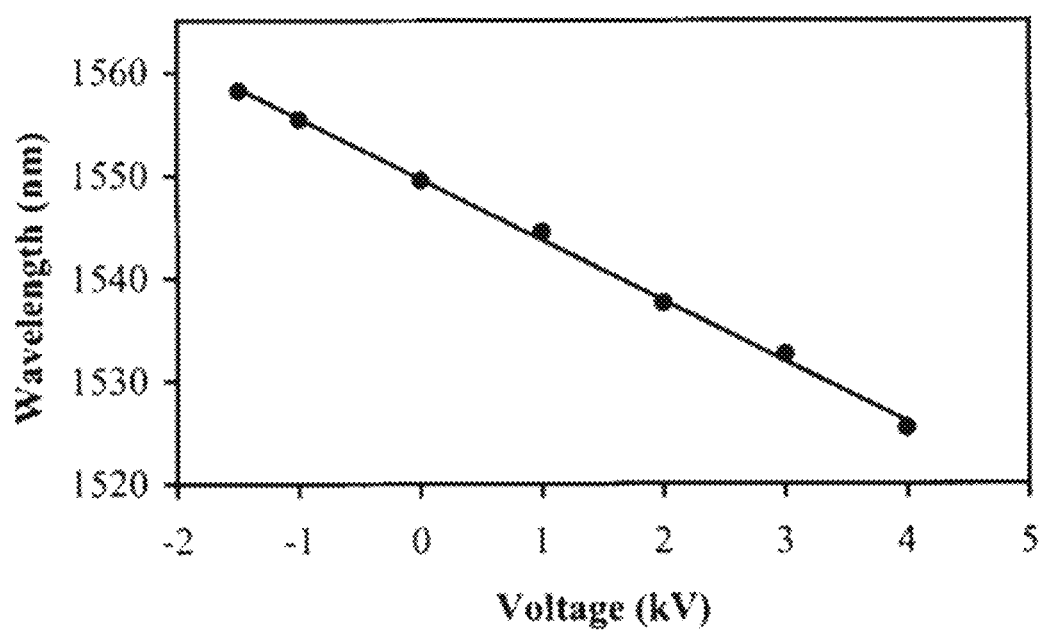
FIG. 10 illustrates how modulating voltage can control a light emitter's output.

Modulating voltage is yet another option to control the light emitter output. Joanna L. Casson, et al. demonstrated turnability of a near-IR through implementation of an integrated LiTaO3 deflector in combination with a reflection grating as an electronically tunable filter. The performance of this voltage control methodology is shown in FIG. 10 which plots with wavelengths from 1527 nm up to 1558 nm vs applied voltage. FIG. 10 is published at Joanna L. Casson, Li Wang, Nathaniel J. C. Libatique, Ravinder K. Jain, David A. Scrymgeour, Venkatraman Gopalan, Kevin T. Gahagan, Robert K. Sander, and Jeanne M. Robinson, "Near-IR tunable laser with an integrated LiTaO3 electro-optic deflector," Appl. Opt. 41, 6416-6419 (2002), the disclosure of which is specifically incorporated herein by reference.

Another voltage control methodology involves Surface Plasmon Resonance (SPR) with potential for device miniaturization and low power consumption. In that light emitting sources can be manufactured from many materials by many techniques including but not limited to thermo-optic, magneto-optic, acousto-electric, and acousto-optic methods to control the delivered wavelength(s), we believe the primary methods described here are the simplest, most efficient, and lowest cost to implement.

With these various control options in our tool set, we can develop light energy input control protocols based upon inputs on the environmental temperature, skin temperature, and nature of the target and interfering analytes absorption behaviors over specified operating ranges for the test sample or test site. The absorption behavior data sets must be generated from complex tissue phantoms and mammalian testing.

Figure 11:
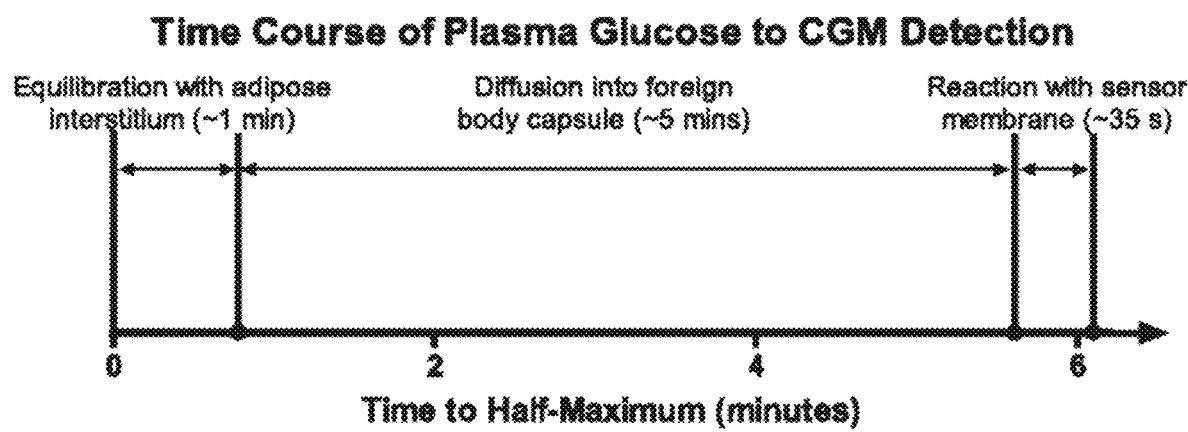
FIG. 11 illustrates the lag time for glucose to migrate from capillaries to interstitial fluid. Ref: Fibrotic Encapsulation Is the Dominant Source of Continuous Glucose Monitor Delays P. Mason McClatchey, 1 Ethan S. McClain, 2 Ian M. Williams, 1 Carlo M. Malabanan, 3 Freyja D. James, 1 Peter C. Lord, 4 Justin M. Gregory, 5 David E. Cliffel, 2 and David H. Wasserman1, 3 Diabetes 2019; 68:1892-1901| https://doi.org/10.2337/db19-0229.

With complex tissue phantoms, precision dosing of glucose levels is routine. However, with mammals, procedures involve very precise Oral Glucose Tolerance Test administration coupled with multiple blood draws timed to optical scan measurements. The blood draws should be assayed for glucose levels near immediately with precision instrumentation to confirm glucose levels in capillary blood. This is highly relevant given recent reporting by P. McClatchey, et al. in 2019 that the lag time for glucose to migrate from the capillaries to the interstitial fluid, where our optical interrogation focuses, is very rapid. Their findings plotted in FIG. 11 list equilibration with adipose interstitium as "~1 minute." McClatchey, Ethan S. McClain, +6 authors D. Wasserman, Fibrotic Encapsulation Is the Dominant Source of Continuous Glucose Monitor Delays: 8 Aug. 2019 DOI10.2337/db19-0229 Corpus ID: 199517999, the disclosure of which is specifically incorporated herein by reference. Having sample or mammalian temperature vs wavelength and temperature vs absorbance values is sufficient to build look up tables useful for establishing our light energy input control protocols.

Figure 12:
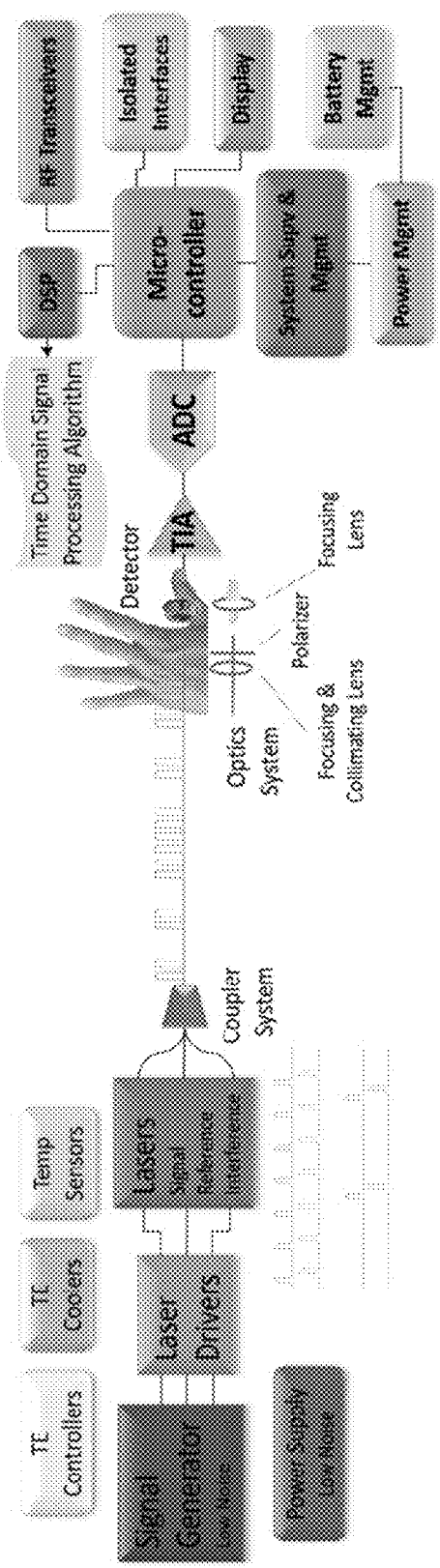
FIG. 12 is a circuit device diagram for driving multiple lasers and coupling the multiple laser outputs into a single path that travels to the interrogation site of the sample or human skin in accordance with the present invention.

FIG. 12 details a typical circuit device diagram for driving multiple lasers and the coupling of the multiple laser outputs into a single path that travels to the interrogation site of the sample or human skin. Emission from the sample or skin is captured with an optical detector with the signal then being amplified and processed for analysis. Prior art primarily focused on the nature of the pulses by way of wavelength, power, pulse duration, frequency. In this invention, we are now focusing on the importance of monitoring temperature variations of the sample or skin and the necessary electro-optics management to precisely match excursions of target analyte and interference analyte(s) absorption peaks over temperature by adjusting the peak center wavelengths of the set of light emission sources.

Figure 13:
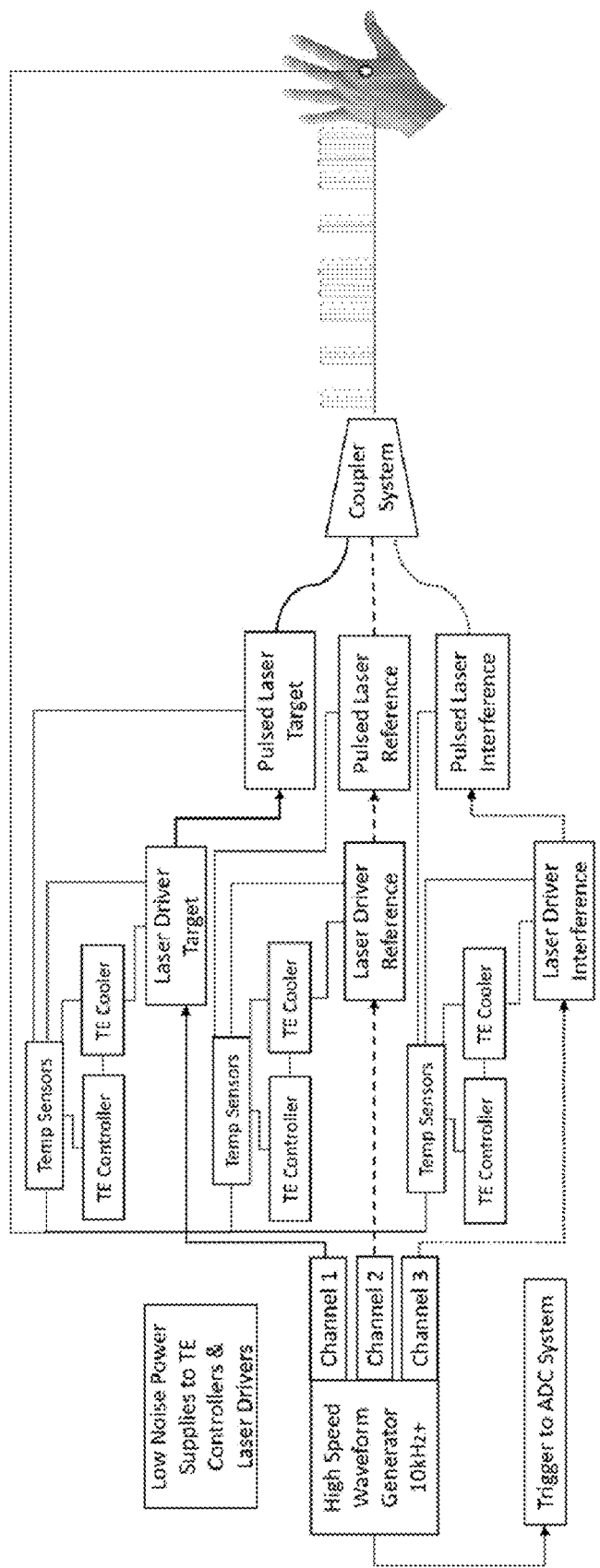
FIG. 13 expands upon FIG. 12 to illustrate how temperature data can be captured for use in the present invention.

FIG. 13 expands the level of detail as to how temperature data is captured to implement this next level of precision monitoring scheme. The multiple points where temperature data is captured and used for constant feedback is shown throughout the sensor electro-optics light emitter delivery system as well as through optical or physical thermocouple contact to the sample or skin under interrogation.

Figure 14:
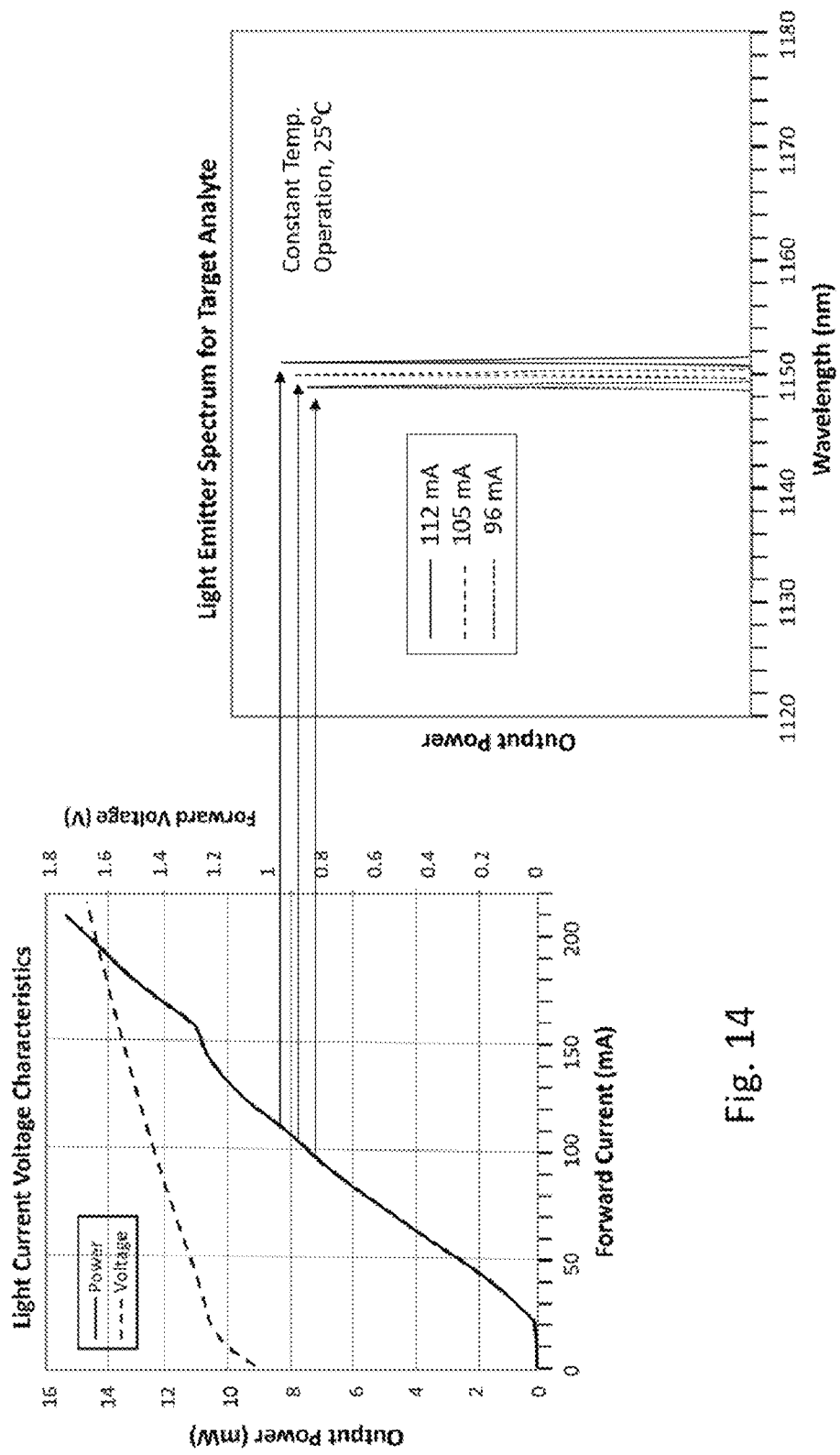
FIG. 14 illustrates how raising applied forward current to a light emitter element can shift the center wavelength of the light emitter element in accordance with the present invention.

One electro-optic control scheme is presented in FIG. 14. In this example, by raising the applied forward current to the light emitter element from 96 mA up to 112 mA, it will shift the center wavelength from 1149 nm up to 1151 nm.

Figure 15:
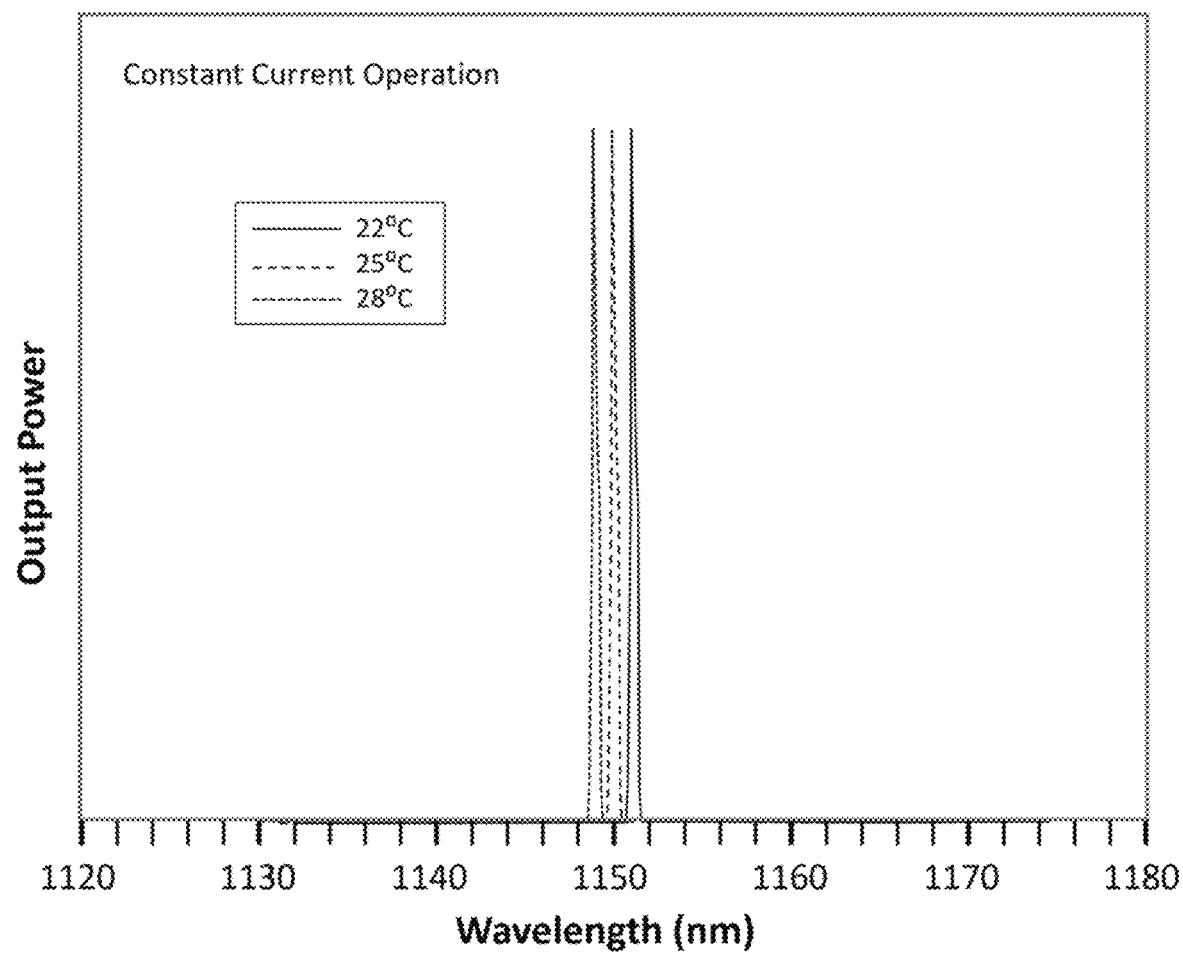
FIG. 15 illustrates how operating under constant current may support keeping the peak output power level over the adjustment range for the center wavelength in accordance with the present invention.

Another electro-optic control scheme light emitter system running under constant current is to use the locally mounted thermo-electric cooler to lower the emitter temperature from 28° C. down to 22° C. causing an emission center wavelength to decrease from 1151 nm down to 1149 nm. As shown in FIG. 15, operating under constant current may support keeping the peak output power level over the adjustment range for the center wavelengths.

There exist many other control schemes for modulating the center wavelength and they should each be selected based on a combination of goals for minimizing size, ease of manufacturing, and cost while maximizing energy efficiency, especially for battery operated sensor systems.

The goal of this disclosure is developing an even more efficient electro-optic system that actively monitors the temperature of the sample or skin and has sufficient feedback controls to identify when and by how much a temperature change will affect the focus absorption peaks or bands of the analytes being measured. Then, through a database that might present as a look up table, determinations can be made, dynamically, to change the electro-optic controls for the output light emitters such that their center wavelengths track to the target and interference analyte(s) for implementing the highest precision absorption spectroscopy system already employing noise cancellation methodology as disclosed in earlier work.

Figure 16:
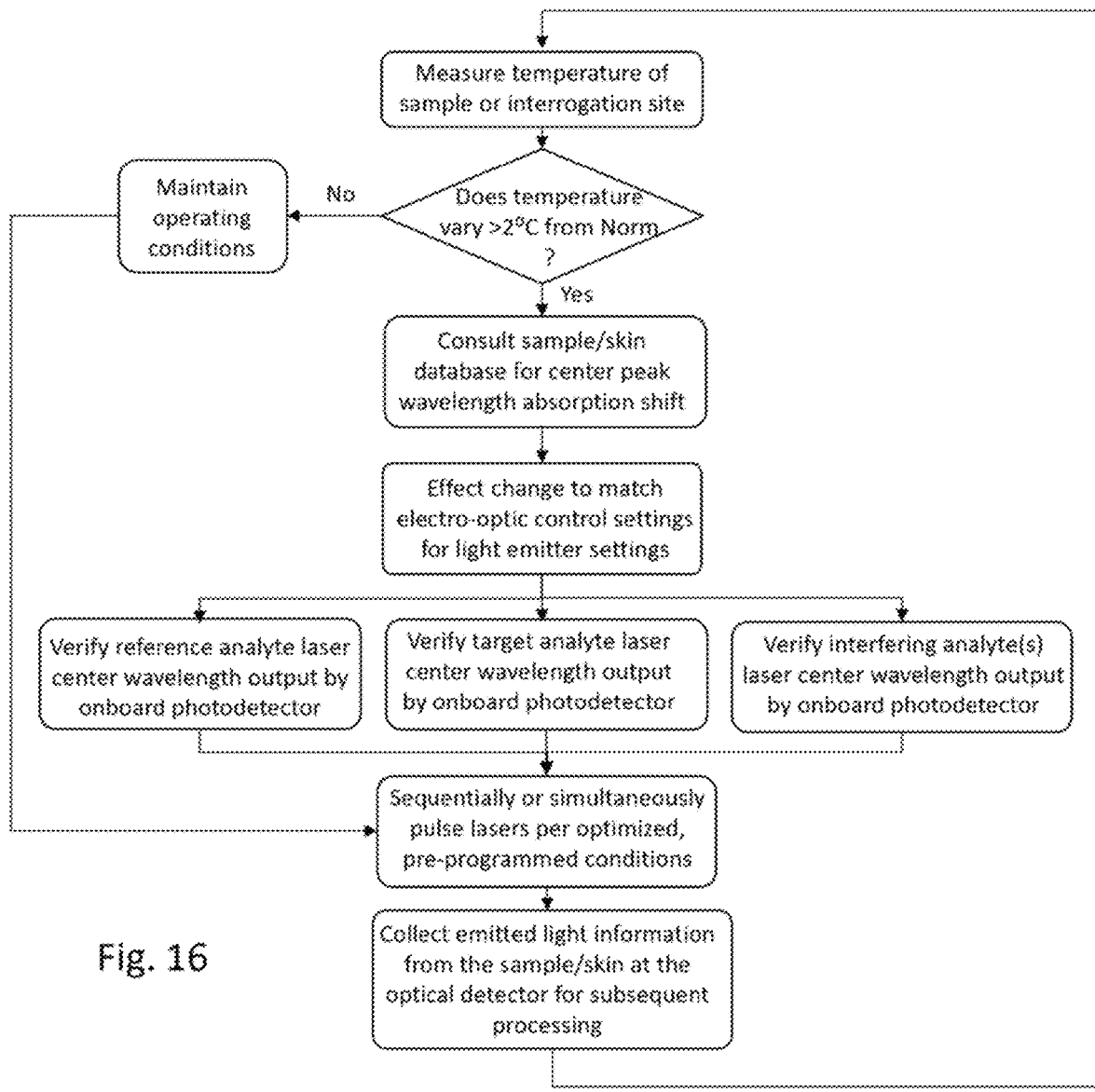
FIG. 16 is one example of a temperature feedback control scheme in accordance with the present invention.

One example of such a temperature feedback control scheme is presented in FIG. 16. Either by spot monitoring or continuous monitoring, the sample or skin temperature is measured and input to the dynamic control system. In this example, a 2° C. change in temperature of the sample/skin is chosen as an indicator to implement dynamic modulation of the Reference, Target ASAP, and Interfering ASAP light emitter center peak wavelengths output for optimizing the precision or our absorption spectroscopy monitoring function. As shown in the flow chart, the wavelength tuning process may rely upon photodetectors that actively measure the output of each light emitter source. The whole tuning function may rely upon a preprogrammed calibration table or a customized calibration table that specifies a certain operating set of parameters to create the desired output wavelength pattern for each emitting source. The use of a 2° C. change in temperature is merely illustrative and the actual threshold for change may vary, both in the upward and downward direction, based upon empirical results.

Figure 17:
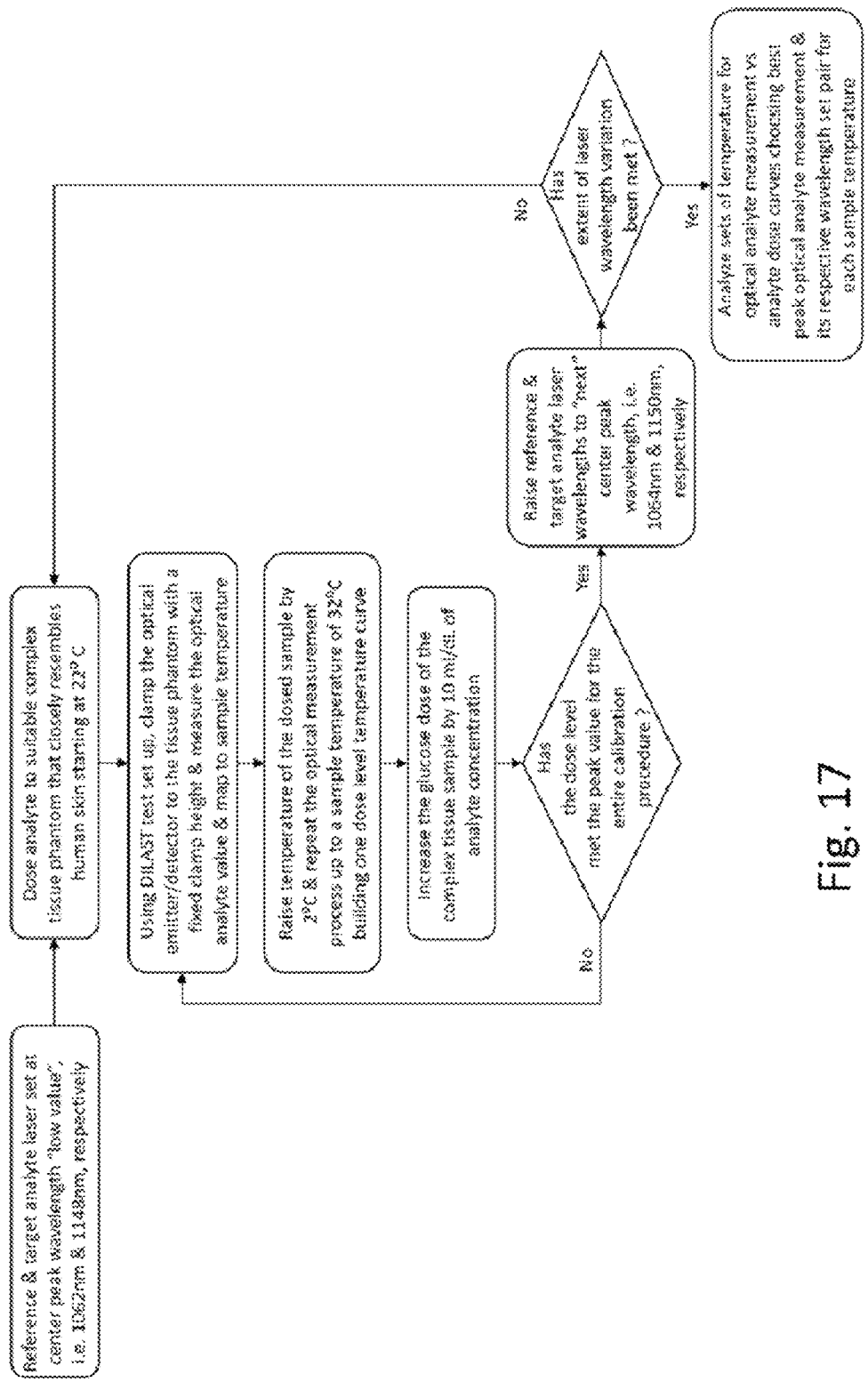
FIG. 17 is a flow chart illustrating a calibration process which can be used to establish temperature baseline peak absorption standards.

FIG. 17 provides an exemplary description of a calibration process to establish temperature baseline peak absorption standards. In this example, it is assumed that the signal beam includes 1,150 nm. This equipment system calibration process may be run on one or several types of complex tissue phantoms that closely resemble human skin. With the advent of 3-D printing of biological-like materials, the science is ever more closely approaching the creation of truly replicant human tissue with the benefit of being able to progressively dose the tissue phantoms with increasing concentrations of the target analyte. For each dose level and at each chosen temperature condition, it is possible to run the proscribed absorption spectroscopic measurement of a controlled interrogation volume to output a representative sensor value that matches to the original tissue phantom dose value.

Figure 18A:
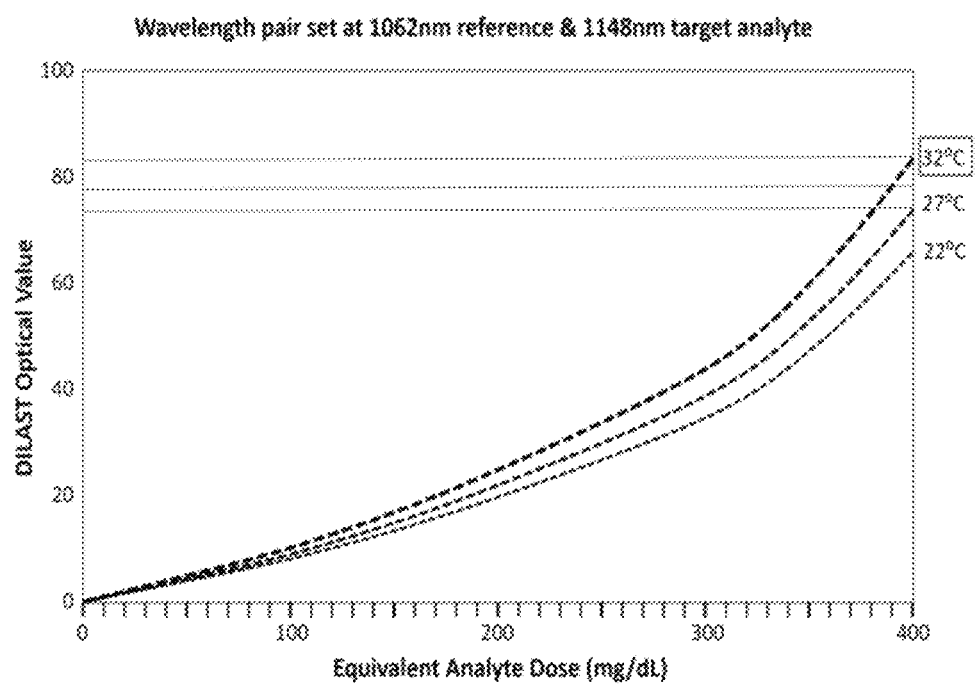
FIGS. 18A-C are a theoretical compiled database of DILAST optical value versus sample analyte concentration for three reference and target analyte center peak wavelength pairs.
Figure 18B:
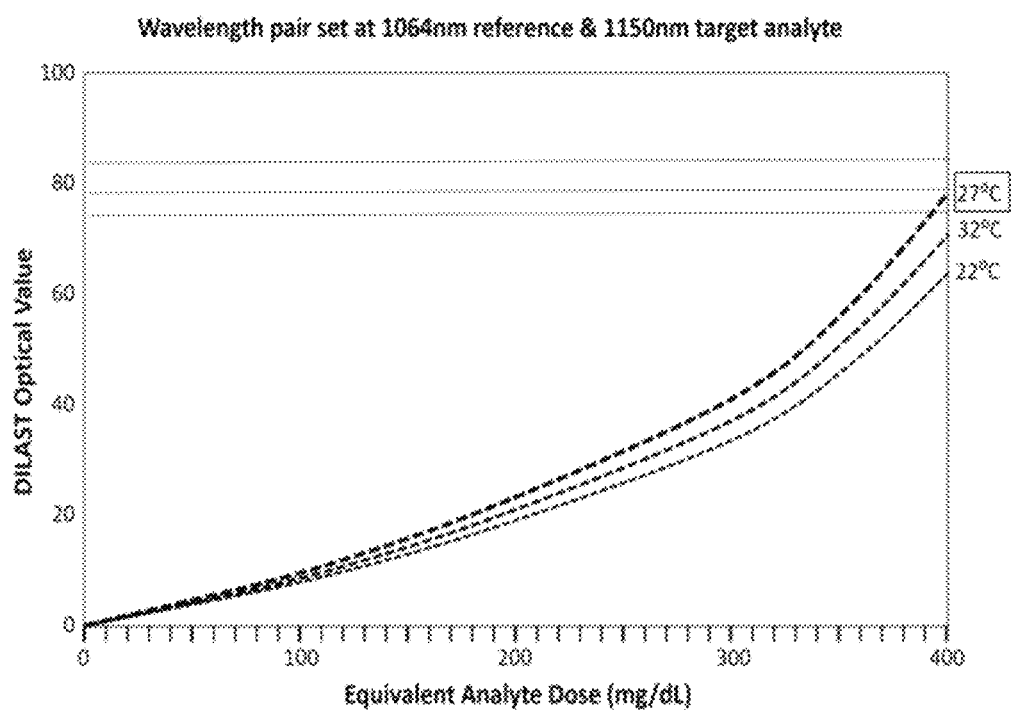
Figure 18C:
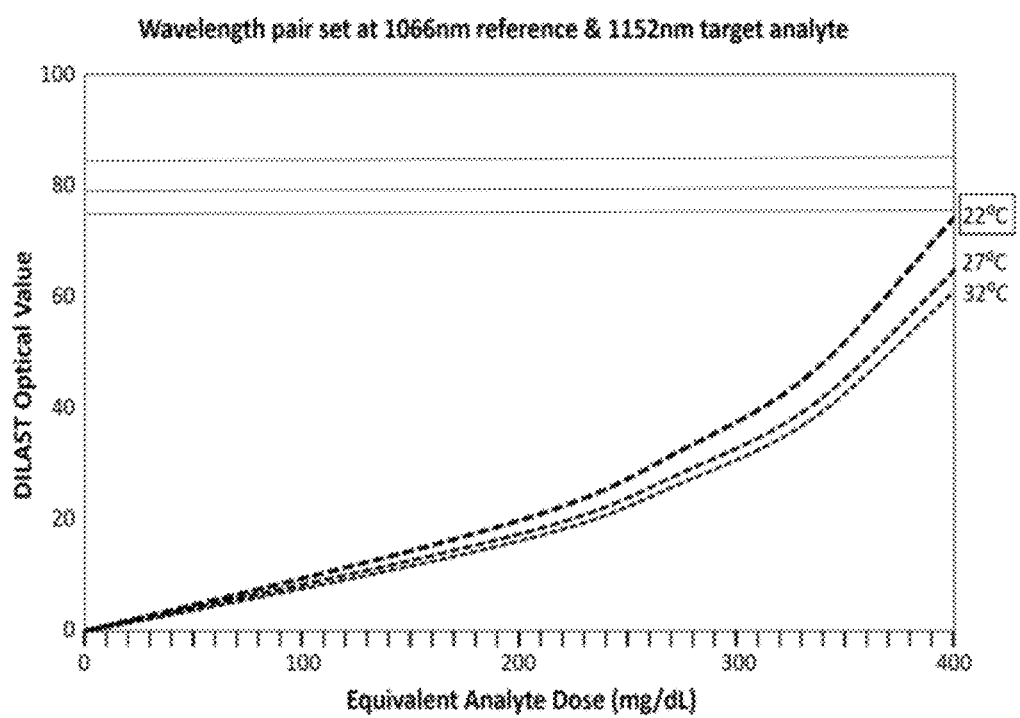

The example presented in FIGS. 18A-C represents a theoretical compiled database of DILAST optical values versus sample analyte concentration for three reference and target analytes center peak wavelength pairs. The wavelength pairs in FIG. 18A are a "low" set of 1062 nm reference emitter and 1148 nm target analyte emitter wavelengths where the expected highest level of optical absorption values are seen at the highest environmental skin temperature of 32° C.

The wavelength pairs in FIG. 18B are a "medium" set of 1064 nm reference emitter and 1150 nm target analyte emitter wavelengths where the expected highest optical absorption values are recorded at a mid-level environmental skin temperature level of 27° C.

The wavelength pairs in FIG. 18C are a "high" set of 1066 nm reference emitter and 1152 nm target analyte emitter wavelengths where the expected highest optical absorption values are recorded at a low-level environmental skin temperature level of 22° C.

This spectroscopic absorption level versus tissue phantom dose levels database supports the sensor system protocols for real world matching of the optimum emitter wavelength pairing, i.e., highest absorption level for greatest sensitivity for precision analyte measurement, to the sample or human skin temperature under evaluation.

Striving for the utmost possible accuracy with our DILAST sensing system may seem extreme, but in dealing with human skin, for example, there are numerous variables involved making precise, repeatable, and reliable analyte concentration measurements difficult. By incorporation of this level of precision to optimize optical, non-invasive, absorption spectroscopy, the overall tolerances can be minimized given that a number of variables in human skin exist.

With such a database of optimized emitter wavelength pairs versus temperature, progression to deployment of highest precision DILAST-based monitors for humans is supported. An element to deploying this system with humans, initially, will involve trained medical professionals implementing an Oral Glucose Tolerance Test (OGTT) with their patients. Please note that it is anticipated typical physician office temperatures will be in the "medium" range of temperatures that will support a human skin temperature of 27° C.

Figure 19:
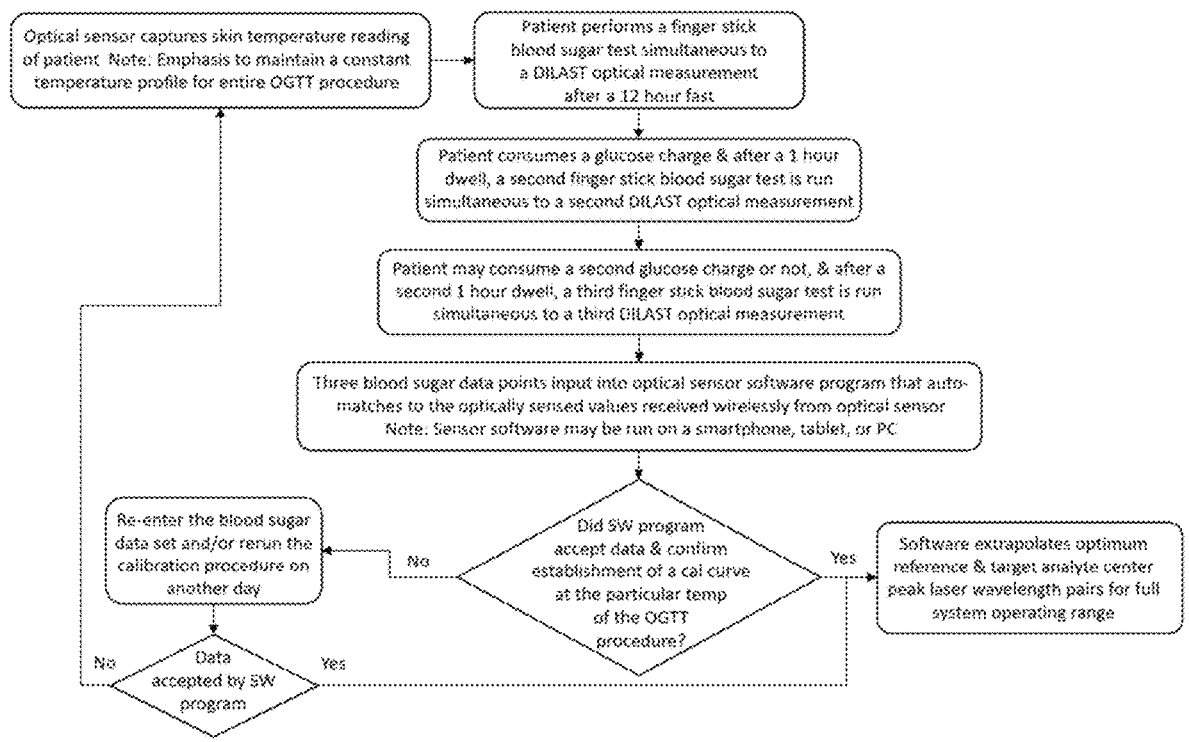
FIG. 19 is a flowchart which illustrates Patient Oral Glucose Tolerance Test (OGTT) calibration at one temperature extrapolated for optimized operating conditions at balance of operating temperature range.

With the reference and target analyte emitter wavelength pairs set for this office calibration process, calibration data can now be captured through the flow chart of a typical process in FIG. 19. This flowchart illustrates Patient OGTT calibration at one temperature extrapolated for optimized operating conditions at balance of operating temperature range. This set of steps describes how an OGTT is implemented at one temperature. The "at least three" data points obtained establishes a calibration curve for the individual/patient enabling the DILAST system to overcome the compilation of variables for each human subject.

This calibration curve is not necessarily fixed where active monitoring for changes in human skin conditions calls into action dynamic modifications to the calibration curve to maintain the highest precision in analyte measurement.

Figure 20:
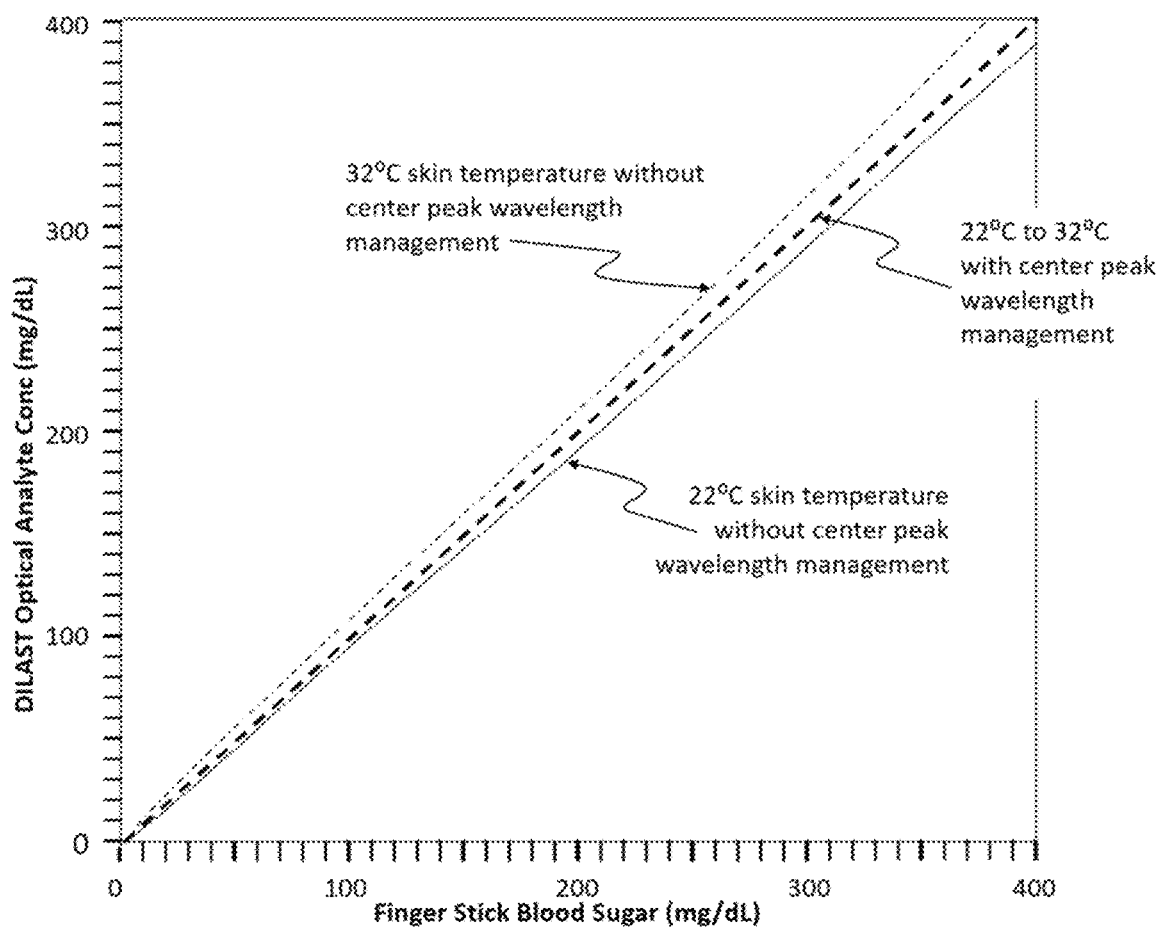
FIG. 20 is a theoretical chart illustrating the effectiveness of OGTT calibration to individual patient and wavelength management for precision sensing.

Presented in FIG. 20 is a theoretical chart illustrating the effectiveness of OGTT calibration to individual patient and wavelength management for precision sensing. The "fine tuning" of our DILAST temperature modulation delivers high accuracy to the medical, sports, and nutrition worlds upon which the best decisions can be made with fine granularity for the utmost in healthcare, athletic performance, and balancing of dietary intake to match with gut biome functions for living longer and stronger.

The present invention is not meant to be limited to control regimes for narrow band light emitter sources to those described here. Most experience is with discrete light emitter sources that are fully characterized and sorted for their performance to optimize system yield and minimize challenges in calibration of production systems. Other control regimes may involve fully integrated light emitters on a single platform. Having more intimate access to the individual light emitter circuits on a single substrate affords employment of smaller form factor emitter modulation schemes. The modulation schemes can include acousto-optic modulation which is typically employed with constant wave output of light sources.

Figure 21:
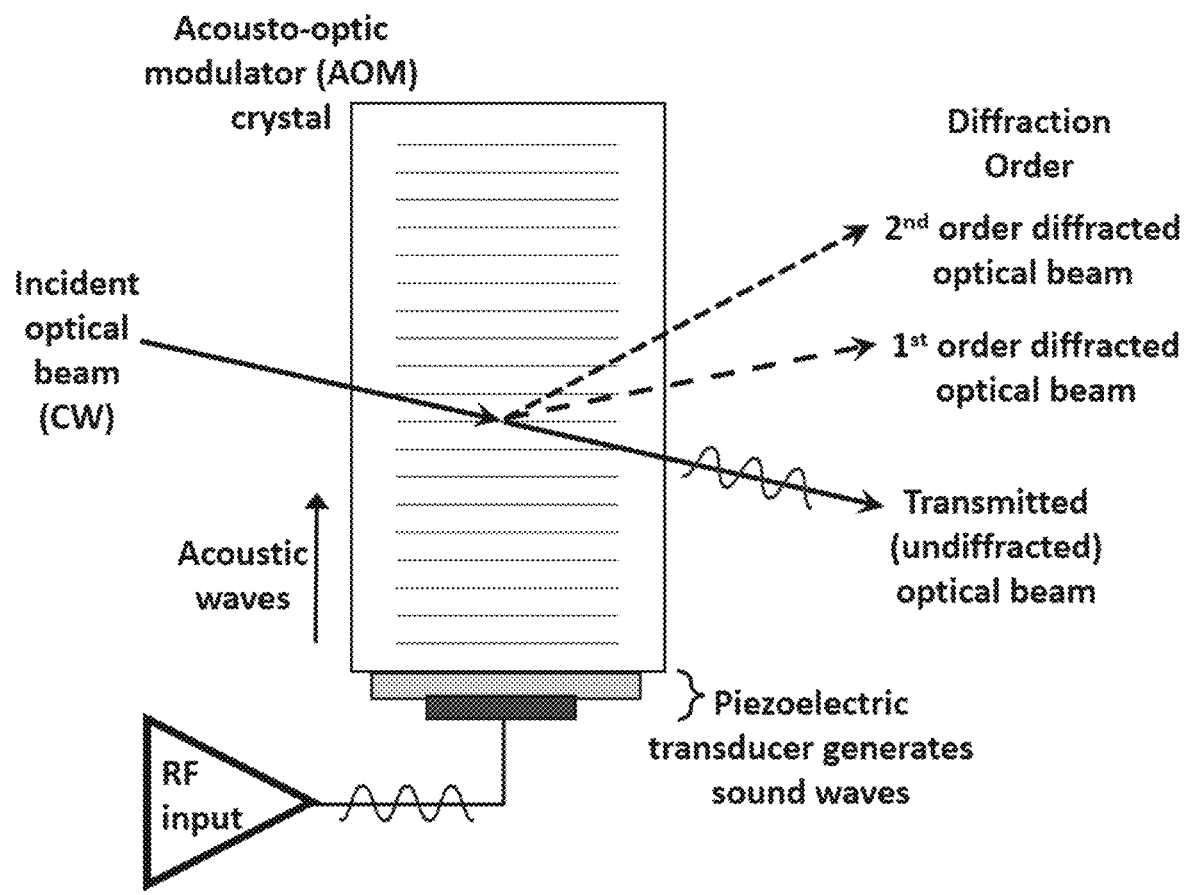
FIG. 21 is a schematic of a typical solid-state Acousto-Optic Deflector (AOD) operating with a standing acoustic wave that is generated by a laser beam incident at the Bragg angle to the AOD.

FIG. 21 provides a schematic of a typical solid-state acousto-optic modulator operating with a standing acoustic wave in the Bragg regime. This portrayal is an up-shifted diffraction. By varying the acoustic frequency input to the piezoelectric transducer, the incident optical beam is diffracted establishing first and second order diffracted optical beams. In the random-access mode of operation, the acoustic frequency is changed discretely from one to another to access random positions. In the continuous scan mode of operation, the acoustic frequency is varied continuously so that the deflection angle changes continuously. Zeng et al. (2009) https://doi.org/10.1063/1.2409868.

For particularly high modulation bandwidths e.g., in the gigahertz region, integrated optical traveling-wave modulators are used. The electric drive signal generates an electromagnetic wave (microwave) propagating along the electrodes in the direction of the optical beam. Matching phase velocities of both waves through an appropriate electrode design establishes efficient modulation. Typical modulations for our range of optical interrogation would vary from 200 GHz up to 300 GHz.

Accordingly, the present invention recognizes that it is desirable to determine the temperature of the liquid sample (by an appropriate temperature sensing means) and compare this temperature to a design (or standardized) temperature for beams used in the absorption spectroscopy process. If the temperature of the liquid sample is within a preselected temperature variation from the standardized temperature, then the beams used in the absorption spectroscopy process (which might be either a signal beam with a reference beam or a signal beam and an interference beam with a reference beam) can be used without any adjustment to their center wavelength associated with the standardized temperature. However, if the temperature of the liquid sample is outside of the preselected temperature variation from the standardized temperature, then the beams used in the absorption spectroscopy process (either the signal beam or the signal and interference beams) will need to be adjusted so that a temperature adjusted signal center wavelength is used for the signal bandwidth and, if an interference beam is being used, so that a temperature adjusted interference center wavelength is used for the interference bandwidth. The means for adjusting the signal center wavelength (and, if being used, the interference center wavelength) will vary depending upon the type of hardware being used in the absorption spectroscopy process and designer choice, but the adjustments will be relatively subtle, in the approximate range of up to a couple of nm, which can be achieved through various techniques for modulating the light emitter source(s), as well as other techniques, examples of which include acousto-optic, acousto-electronic, magneto-optic, Surface Plasmon Resonance, and variable pressure gaseous chambers. The important point is that increased precision is obtained by recognizing the effect of temperature of the liquid sample, especially for human in vivo testing, which can vary depending upon environmental and other factors, and then slightly adjusting the center wavelengths of critical beams used in the process, to obtain more precise results. This is especially true for detection of glucose molecules in humans when the absorption spectroscopy process is using a signal beam with an absorption band which includes 1,150 nm and a reference beam which includes 1,064 nm.

It is also worth noting that the center wavelength of the reference beam can also be adjusted to a temperature adjusted reference center wavelength if the absorption band of the reference beam is narrow enough to require temperature adjustment so as to maintain precision results. When glucose molecules in humans are being detected by an absorption spectroscopy process using a signal beam with an absorption band which includes 1,150 nm and a reference beam which includes 1,064 nm, it is desirable to also adjust the center wavelength of the reference beam to a temperature adjusted reference center wavelength when the center wavelength of the signal beam is adjusted to a temperature adjusted signal center wavelength.

While the invention described herein with reference to certain preferred embodiments, these embodiments have been presented by way of example only, and not to limit the scope of the invention. Additional embodiments thereof will be obvious to those skilled in the art having the benefit of this detailed description. Further modifications are also possible in alternative embodiments without departing from the inventive concept.

What is claimed is:

1. A process for quantifying a concentration of a targeted molecule in a liquid sample through use of an absorption spectroscopy process, comprising:
measuring a liquid sample temperature; and
if the liquid sample temperature is within a preselected temperature variance from a standardized temperature, using a preselected signal center wavelength for a signal bandwidth; or
if the liquid sample temperature is outside of the preselected temperature variance from the standardized temperature, using a temperature adjusted signal center wavelength for the signal bandwidth, wherein the temperature adjusted signal center wavelength is different than the preselected signal center wavelength and is adjusted from the preselected signal center wavelength based upon the liquid sample temperature being outside of the preselected temperature variance;

wherein the absorption spectroscopy process is comprised of:
pulsing a signal beam with a signal pulsed source;
pulsing a reference beam with a reference pulsed source;
spatially combining the pulsed signal beam and the pulsed reference beam into a single radiation beam which passes into the liquid sample;
detecting a pulsed signal beam output and a pulsed reference beam output after the single radiation beam passes out of the liquid sample;
processing the pulsed signal beam output and the pulsed reference beam output to obtain a value over a preselected period of time; and
calculating a concentration level of the targeted particle in the liquid sample based on the value;
wherein the signal pulsed source emits radiation at the signal bandwidth which is coincident with an absorption band of the targeted particle while the reference pulsed source emits radiation at a reference wavelength which is not coincident with the absorption band; and
wherein the signal pulsed source is separate from the reference pulsed source.

2. The process of claim 1, wherein the liquid sample is an in vivo human sample and the liquid sample temperature is measured by measuring a temperature associated with the in vivo human sample.

3. The process of claim 2, wherein the signal beam includes 1,150 nm.

4. The process of claim 3, wherein the temperature adjusted signal center wavelength for the signal bandwidth is obtained by a technique for modulating a light emitter source for the signal beam.

5. The process of claim 3, wherein the difference between the preselected signal center wavelength and the temperature adjusted signal center wavelength is approximately 2 nm or less.

6. The process of claim 3, wherein:
if the liquid sample temperature is within the preselected temperature variance from the standardized temperature, using a preselected reference center wavelength for a reference bandwidth; or
if the liquid sample temperature is outside of the preselected temperature variance from the standardized temperature, using a temperature adjusted reference center wavelength for the reference bandwidth, wherein the temperature adjusted reference center wavelength is different than the preselected reference center wavelength and is adjusted from the preselected reference center wavelength based upon the liquid sample temperature being outside of the preselected temperature variance.

7. The process of claim 1, wherein:
if the liquid sample temperature is within the preselected temperature variance from the standardized temperature, using a preselected reference center wavelength for a reference bandwidth; or
if the liquid sample temperature is outside of the preselected temperature variance from the standardized temperature, using a temperature adjusted reference center wavelength for the reference bandwidth, wherein the temperature adjusted reference center wavelength is different than the preselected reference center wavelength and is adjusted from the preselected reference center wavelength based upon the liquid sample temperature being outside of the preselected temperature variance.

8. A process for quantifying a concentration of a targeted molecule in a liquid sample through use of an absorption spectroscopy process, comprising:
measuring a liquid sample temperature; and
if the liquid sample temperature is within a preselected temperature variance from a standardized temperature, using a preselected signal center wavelength for a signal bandwidth and a preselected interference central wavelength for an interference bandwidth;
if the liquid sample temperature is outside of the preselected temperature variance from the standardized temperature, using a temperature adjusted signal center wavelength for the signal bandwidth and a temperature adjusted interference center wavelength for the interference bandwidth;
wherein the absorption spectroscopy process is comprised of:
pulsing a signal beam with a signal pulsed source;
pulsing a reference beam with a reference pulsed source;
pulsing an interference beam with an interference pulsed source;
spatially combining the pulsed signal beam, the pulsed reference beam, and the pulsed interference beam into a single radiation beam which passes into the liquid sample;
detecting a pulsed signal beam output, a pulsed reference beam output, and a pulsed interference beam output after the single radiation beam passes out of the liquid sample;
processing the pulsed signal beam output and the pulsed reference beam output to obtain a first value over a first preselected period of time;
processing the pulsed interference beam output and the pulsed reference beam output to obtain a second value over a second preselected period of time;
using the second value to obtain a calibration curve adjustment representative of optical interference represented by the at least one interfering molecule concentration; and
calculating a concentration level of the targeted particle in the liquid sample based on the first value and the calibration curve adjustment;
wherein the signal pulsed source emits radiation at the signal bandwidth which is coincident with an absorption band of the targeted particle and the interference pulsed source emits radiation at the interference bandwidth which is coincident with a second absorption band of the at least one interfering molecule while the reference pulsed source emits radiation at a reference wavelength which is not coincident with the absorption band or the second absorption band.

9. The process of claim 8, wherein the liquid sample is an in vivo human sample and the liquid sample temperature is measured by measuring a temperature associated with the in vivo human sample.

10. The process of claim 9, wherein the signal beam includes 1,150 nm.

11. The process of claim 10, wherein the temperature adjusted signal center wavelength for the signal bandwidth is obtained by a technique for modulating a light emitter source for the signal beam.

12. The process of claim 10, wherein the difference between the preselected signal center wavelength and the temperature adjusted signal center wavelength is approximately 2 nm or less.

13. The process of claim 10, wherein:
- if the liquid sample temperature is within the preselected temperature variance from the standardized temperature, using a preselected reference center wavelength for a reference bandwidth; or
- if the liquid sample temperature is outside of the preselected temperature variance from the standardized temperature, using a temperature adjusted reference center wavelength for the reference bandwidth, wherein the temperature adjusted reference center wavelength is different than the preselected reference center wavelength and is adjusted from the preselected reference center wavelength based upon the liquid sample temperature being outside of the preselected temperature variance.

14. The process of claim 9, wherein:
- if the liquid sample temperature is within the preselected temperature variance from the standardized temperature, using a preselected reference center wavelength for a reference bandwidth; or
- if the liquid sample temperature is outside of the preselected temperature variance from the standardized temperature, using a temperature adjusted reference center wavelength for the reference bandwidth, wherein the temperature adjusted reference center wavelength is different than the preselected reference center wavelength and is adjusted from the preselected reference center wavelength based upon the liquid sample temperature being outside of the preselected temperature variance.

* * * * *